(12) United States Patent
Yoshimura

(10) Patent No.: US 7,977,393 B2
(45) Date of Patent: Jul. 12, 2011

(54) COMPOSITION CONTAINING OXOCARBON AND USE THEREOF

(75) Inventor: Ken Yoshimura, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 629 days.

(21) Appl. No.: 11/813,538

(22) PCT Filed: Jan. 10, 2006

(86) PCT No.: PCT/JP2006/300405
§ 371 (c)(1),
(2), (4) Date: Aug. 16, 2007

(87) PCT Pub. No.: WO2006/075721
PCT Pub. Date: Jul. 20, 2006

(65) Prior Publication Data
US 2008/0160417 A1    Jul. 3, 2008

(30) Foreign Application Priority Data

Jan. 12, 2005 (JP) ................................. 2005-004957
Feb. 21, 2005 (JP) ................................. 2005-043676
Jun. 17, 2005 (JP) ................................. 2005-177619

(51) Int. Cl.
    *C08J 5/20*  (2006.01)
(52) U.S. Cl. ............... 521/27; 524/82; 524/86; 524/107
(58) Field of Classification Search ................ 521/27; 524/82, 86, 107
See application file for complete search history.

(56) References Cited

U.S. PATENT DOCUMENTS

| | | | |
|---|---|---|---|
| 4,069,201 A * | 1/1978 | Mark ............................ | 524/358 |
| 5,403,675 A | 4/1995 | Ogata et al. | |
| 5,438,082 A | 8/1995 | Helmer-Metzmann et al. | |
| 5,525,436 A | 6/1996 | Savinell et al. | |
| 5,985,477 A | 11/1999 | Iwasaki et al. | |
| 6,004,698 A * | 12/1999 | Richardson et al. .......... | 429/305 |
| 2003/0013602 A1 | 1/2003 | Uchida et al. | |
| 2005/0131105 A1 | 6/2005 | Choate et al. | |

FOREIGN PATENT DOCUMENTS

| | | |
|---|---|---|
| CN | 1411617 A | 4/2003 |
| JP | 50-098538 A | 8/1975 |
| JP | 55-161377 A | 12/1980 |
| JP | 10-021943 A | 1/1998 |
| JP | 11-503262 A | 3/1999 |
| JP | 11-340097 A | 12/1999 |
| JP | 2003-277501 A | 10/2003 |
| JP | 2003-301105 A | 10/2003 |

OTHER PUBLICATIONS

Lowell M. Schwartz, et al. Physical Chemistry of Aqueous Oxocarbons, Academic Press, Inc., 1980, pp. 43-57.
Elizabeth Patton, et al. "New Aromatic Anions. X. Dissociation Constants of Substituted Oxocarbon Acids" Journal of the American Chemical Society, 1973, vol. 95, No. 26, pp. 8703-8707.
R. Nolte, et al. "Partially sulfonated poly (arylene ether sulfone)—A versatile proton conducting membrane material for modern energy conversion technologies" Journal of Membrane Science, 1993, vol. 83, pp. 211-220.
Allcock, et al. "Sulfonation of (Aryloxy) and (Arylamino) phosphazenes: Small-Molecule Compounds, Polymers, and Surfaces" Chemistry of Materials, 1991, vol. 3, No. 6, pp. 1120-1132.
Lanny S. Liebeskind, et al. "An Improved Method for the Synthesis of Substituted Cyclobutenediones" Journal of Organic Chemistry, 1988, vol. 53, No. 11, pp. 2482-2488.
David L. Selwood, et al. "A New, Efficient Synthesis of 5-Undecyl-6-Hydroxy-4, 7-Dioxobenzothiazole (UHDBT), A Potent Electron Transport Inhibitor" Heterocycles, 1988, vol. 27, No. 5, pp. 1191-1196.
Lanny S. Liebeskind, et al. 3-Stannylcyclobutenediones as Nucleophilic Cyclobutenedione Equivalents . . . Journal of Organic Chemistry, 1990, vol. 55, No. 19, pp. 5359-5364.
Lanny S. Liebeskind, et al. "Synthesis of Substituted Cyclobutenediones by the Paladium Catalyzed . . . " Tetrahedron Letters, 1990, vol. 31, No. 30, pp. 4293-4296.
Green, et al. "Synthesis of 1, 2-Diphenylcyclobutene-3,4-dione", 1974, pp. 46-47.
J.S. Wainwright, et al. "Acid-Doped Polybenzimidazoles: A New Polymer Electrolyte" Journal of the Electrochemical Society, 1995, vol. 142, No. 7, pp. L121-L123.
Reed, et al. "Synthesis of 4-Substitued-3-alkoxy-3-cyclobutene-1-2-diones" Journal of Organic Chemistry, 1988, vol, 53, No. 11, pp. 2477-2482.
Arthur H. Schmidt, et al., Oxokohlenstoffe and verwandte Verbindugen, Synthesis, 1991, No. 7, pp. 579-582.

* cited by examiner

*Primary Examiner* — Edward J Cain
(74) *Attorney, Agent, or Firm* — Sughrue Mion, PLLC

(57) ABSTRACT

Provided is a polymer composition containing an oxocarbon and a polymer, further, a polymer composition that the oxocarbon are expressed by formula (1).

31 Claims, No Drawings

COMPOSITION CONTAINING OXOCARBON AND USE THEREOF

TECHNICAL FIELD

The present invention relates to a composition containing an oxocarbon and the use thereof.

BACKGROUND ART

It is known that oxocarbons typified by squaric acid have high acidity because its structure that hydrogen has been dissociated from an oxocarbon group is stabilized by resonance (Oxocarbons, p. 45 (Edited by Robert West), Academic, Press (1980), (ISBN: 0-12-744580-3)) (Journal of the American Chemical Society, 95, 8703 (1973)).

On the other hand, for example, a polymer compound having a sulfonic acid group is known as a polymer electrolyte useful in a polymer electrolyte type fuel cell etc. For example, there have been proposed, as polymer electrolytes useful in a polymer electrolyte type fuel cell etc., a fluorinated polymer such as Nafion (trademark of Du Pont Corporation), a polymer that a sulfonic acid group is introduced into polyetherketones (U.S. Pat. No. 5,433,082), a polymer that a sulfonic acid group is introduced into polyethersulfones (J. Membrane Science, 83, 211 (1993)), a polymer that a sulfonic acid group is introduced into polyimides (Japanese Patent Application 2003-277501), a polymer that a sulfonic acid group is introduced into polyphenylenes (U.S. Pat. No. 5,403,675), and a polymer that a sulfonic acid group is introduced into polyphosphazenes (Chemical Material, 3, 1120 (1991) 4).

Further, in a fuel cell repeating start and stop, it is known that a polymer electrolyte membrane is dilated with water generated in operation and shrinks due to drying in shutoff, causing a dimensional change.

DISCLOSURE OF THE INVENTION

However, a polymer composition containing an oxocarbon and a polymer has not been known yet. The present inventors produced compositions containing an oxocarbon in polymer electrolyte and studied in various ways. As a result, they have found the following and completed the present invention: a composition containing an oxocarbon is useful as a material for proton conductive membrane i.e. polymer electrolyte in a solid polymer type fuel cell using gas fuels such as hydrogen gas and liquid fuels such as methanol and dimethyl ether, and when adding oxocarbons, in comparison with a membrane of a polymer electrolyte alone, flexibility is provided without lowering proton conductivity.

It is an object of the present invention to provide a new composition useful as a material for proton conductive membrane i.e. polymer electrolyte in a solid polymer type fuel cell, and to provide a composition allowing a proton conductive membrane to have higher flexibility than a single polymer electrolyte without lowering proton conductivity, when the composition is processed into the proton conductive membrane.

Namely, the present invention relates to [1] a polymer composition containing an oxocarbon and a polymer.

Further, the present invention is [2] the polymer composition described in [1], wherein the oxocarbon is expressed by the following formula (1):

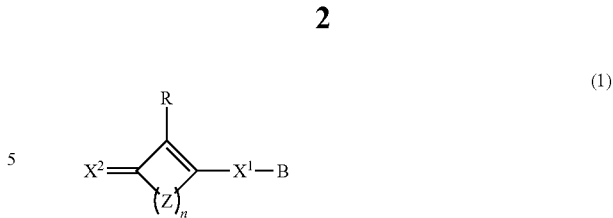

wherein $X^1$ and $X^2$ each independently represent —O—, —S— or —NR'—, Z represents —CO—, —C(S)—, —C(NR")—, an alkylene group having carbon atoms of 1-6 that may have a substituent, or an arylene group having carbon atoms of 6-10 that may have a substituent; n represents the number of Z and an integer of 0 (inclusive) to 10; when Z are plural, each of Z may be the same or different each other; R represents —OH, —SH, —NHR''', an alkyl group having carbon atoms of 1-18 that may have a substituent, an aryl group having carbon atoms of 6-18 that may have a substituent, or an aralkyl group having carbon atoms of 7-16 that may have a substituent; R', R" and R''' each independently represent a hydrogen atom, an alkyl group having carbon atoms of 1-6 that may have a substituent, or an aryl group having carbon atoms of 6-10 that may have a substituent; and B represents a hydrogen atom or a monovalent metal atom.

PREFERRED MODES FOR CARRYING OUT THE INVENTION

The present invention will be described in detail below.

The composition of the present invention is a composition containing an oxocarbon and a polymer. The form of composition is not particularly limited but the composition may be compatible on a molecular level, or may be non-compatible; when the polymer is a membrane, it may be a state where oxocarbons are applied on the surface of the membrane. A compatible form on a molecular level is preferable because of high flexibility of the resultant proton conductive membrane.

Herein, as oxocarbons, for example, those having properties as a proton acid are used, as the example, and there are listed compounds expressed by the following general formula (1):

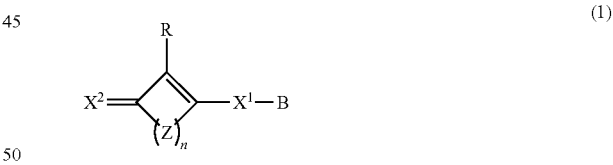

wherein $X^1$ and $X^2$ each independently represent —O—, —S— or —NR'—, Z represents —CO—, —C(S)—, —C(NR")—, an alkylene group having carbon atoms of 1-6 that may have a substituent, or an arylene group having carbon atoms of 6-10 that may have a substituent; n represents the number of Z and an integer of 0 (inclusive) to 10; when Z are plural, each of Z may be the same or different each other; R represents —OH, —SH, —NHR''', an alkyl group having carbon atoms of 1-18 that may have a substituent, an aryl group having carbon atoms of 6-18 that may have a substituent, or an aralkyl group having carbon atoms of 7-16 that may have a substituent; R', R" and R''' each independently represent a hydrogen atom, an alkyl group having carbon atoms of 1-6 that may have a substituent, or an aryl group having carbon atoms of 6-10 that may have a substituent; and B represents a hydrogen atom or a monovalent metal atom.

In oxocarbons expressed by the formula (1), $X^1$ and $X^2$ each independently represent —O—, —S— or —NR'—. R' represents a hydrogen atom; an alkyl group having carbon atoms of 1-6 that may have a substituent typified by methyl, trifluoromethyl, ethyl, propyl, isopropyl, and n-butyl groups, or an aryl group having carbon atoms of 6-10 that may have a substituent typified by phenyl, pentafluorophenyl, and naphthyl groups. R' is preferably a hydrogen atom. $X^1$ and $X^2$ are preferably —O—, —S—, particularly preferably —O—.

Further, Z represents —CO—, —C(S)—, —C(NR")—, an alkylene group having carbon atoms of 1-6 that may have a substituent, or an arylene group having carbon atoms of 6-10 that may have a substituent. R" represents a hydrogen atom; an alkyl group having carbon atoms of 1-6 that may have a substituent typified by methyl, trifluoromethyl, ethyl, propyl, isopropyl, and n-butyl groups, or an aryl group having carbon atoms of 6-10 that may have a substituent typified by phenyl, pentafluorophenyl, and naphthyl groups. R' is preferably a hydrogen atom.

Herein, as an alkylene group having carbon atoms of 1-6, for example, there are listed methylene, ethylene, propylene, 1-propylene, butylene, and pentylene groups. As an arylene group having carbon atoms of 6-10, for example, a phenylene group and a naphthylene group are listed. As a substituent when having a substituent, for example, halogeno groups such as a fluoro group, chloro group, and bromo group are listed, and among them, a fluoro group is preferably used.

Z is preferably —CO—, —C(S)—, —C(NR")—, methylene, difluoromethylene, phenylene, tetrafluorophenylene, more preferably —CO—, —C(S)—, and particularly preferable —CO—.

n represents the number of Z and an integer of 0 (inclusive) to 10. When n is 0, it means a single bond. When Z are plural, each of Z may be the same or different each other. Preferably n is an integer of 0 (inclusive) to 4, more preferably an integer of 0 (inclusive) to 2, and 1 is particularly preferable.

R represents —OH, —SH, —NHR''', an alkyl group having carbon atoms of 1-18 that may have a substituent, an aryl group having carbon atoms of 6-18 that may have a substituent, or an aralkyl group having carbon atoms of 7-16 that may have a substituent. R''' represents a hydrogen atom; an alkyl group having carbon atoms of 1-6 that may have a substituent typified by methyl, trifluoromethyl, ethyl, propyl, isopropyl, and n-butyl groups, or an aryl group having carbon atoms of 6-10 that may have a substituent typified by phenyl, pentafluorophenyl, and naphthyl groups. R''' is preferably a hydrogen atom.

Herein, as an alkyl group having carbon atoms of 1 to 18, for example, there are listed methyl, ethyl, propyl, i-propyl, n-butyl, sec-butyl, isobutyl, t-butyl, pentyl, hexyl, heptyl, octyl, nonyl, decyl, undecyl, dodecyl, tridecyl, tetradecyl, pentadecyl, hexadecyl, heptadecyl, and octadecyl groups.

As a substituent when an alkyl group having carbon atoms of 1 to 18 has a substituent, for example, there are listed a halogeno group such as fluoro group, chloro group and bromo group; a nitro group; a cyano group; an alkoxy group having carbon atoms of 1 to 5 such as methoxy group, ethoxy group and propoxy group; and a fluoroalkyl group having carbon atoms of 1 to 5 such as trifluoromethyl group and pentafluoromethyl group.

Further, as an aryl group having carbon atoms of 6-18, for example, a phenyl group, naphthyl group and anthranil group are listed. As a substituent when an aryl group having carbon atoms of 6-18 has a substituent, there are listed a halogeno group such as fluoro group, chloro group and bromo group; a nitro group; a cyano group; an alkoxy group having carbon atoms of 1 to 5 such as methoxy group, ethoxy group and propoxy group; a fluoroalkyl group having carbon atoms of 1 to 5 such as trifluoromethyl group and pentafluoromethyl group; and an alkyl having carbon atoms of 1 to 5 such as methyl group, ethyl group, propyl group and butyl group.

As an example of the aryl group having carbon atoms of 6-18 having a halogeno group as a substituent, the following formulas (2a) to (2d) are listed:

(2a)

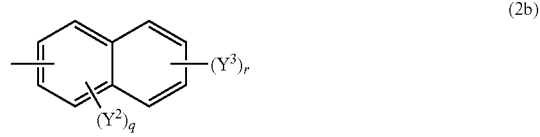

(2b)

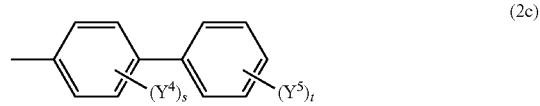

(2c)

wherein $Y^1$ to $Y^5$ each independently represent a halogeno group, p represents an integer of 1 to 5, q represents an integer of 0 (inclusive) to 3, r represents an integer of 0 (inclusive) to 4, and a value of (q+r) is 1 to 7, s represents an integer of 0 (inclusive) to 4, t represents an integer of 0 (inclusive) to 5, and a value of (s+t) is 1 to 9; when $Y^1$ to $Y^5$ are each plural, these may be same or different.

A halogeno group is preferably a fluoro group and a chloro group, particularly preferably a fluoro group. Of (2a) to (2d), (2a) is particularly preferable.

As an aralkyl group having carbon atoms of 7-16, for example, there are listed benzyl, phenylethyl, phenylpropyl, naphthylmethyl, and naphthylethyl groups. As a substituent when an aralkyl having group carbon atoms of 7-16 has a substituent, for example, there are listed a halogeno group such as fluoro group, chloro group and bromo group; a nitro group; a cyano group; an alkoxy group having carbon atoms of 1 to 5 such as methoxy group, ethoxy group and propoxy group; fluoroalkyl group having carbon atoms of 1 to 5 such as trifluoromethyl group and pentafluoromethyl group; and alkyl group having carbon atoms of 1 to 5 such as methyl group, ethyl group, propyl group and butyl group.

R is preferably —OH, —SH, a methyl group, ethyl group, trifluoromethyl group, phenyl group, naphthyl group, pentafluorophenyl group and benzyl group, more preferably —OH, a phenyl group and a pentafluorophenyl group.

B represents a hydrogen atom or a monovalent metal atom. As a monovalent metal, there are listed a lithium atom, sodium atom, potassium atom, cesium atom and silver atom. B is preferably a hydrogen atom, lithium atom, sodium atom, potassium atom and cesium atom, further preferably a lithium atom, sodium atom, potassium atom, and further more preferably a hydrogen atom and a lithium ion.

When the composition of the present invention is used as an electrolyte in a lithium secondary battery, lithium is used as B.

When the composition of the present invention is used in a solid polymer fuel cell, it is preferable when substantially all functional groups are in a free acid form, that is, B is preferably a hydrogen atom.

As specific examples of the oxocarbons expressed by the formula (1) in the present invention, for example, the following compounds are listed. Herein, the case where B is a hydrogen atom is illustrated.

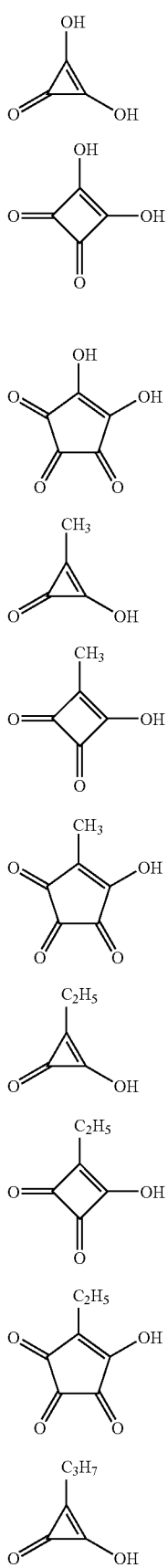
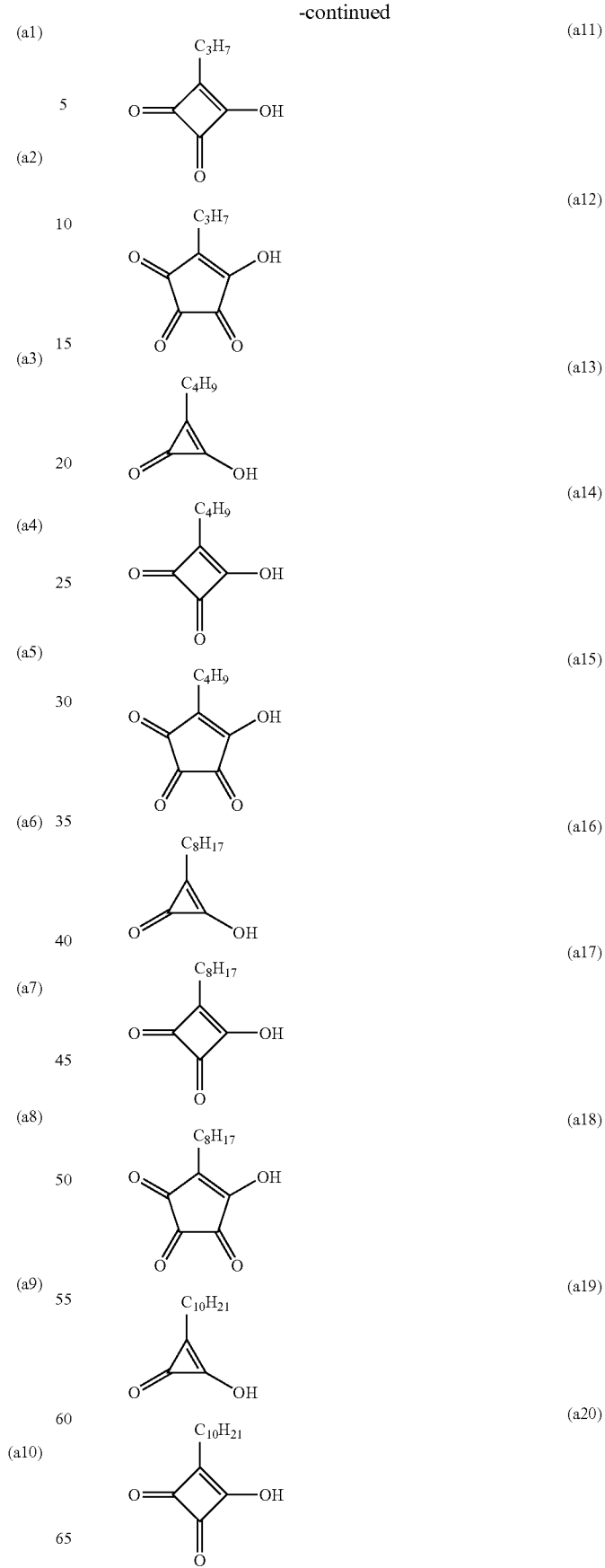

-continued
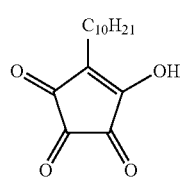 (a21)
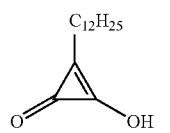 (a22)
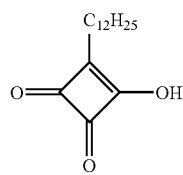 (a23)
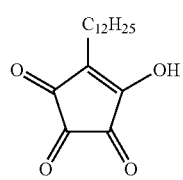 (a24)
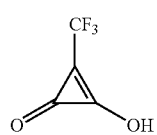 (a25)
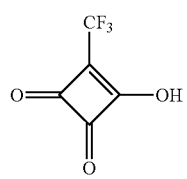 (a26)
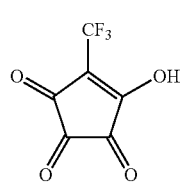 (a27)
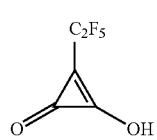 (a28)
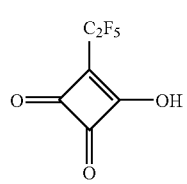 (a29)
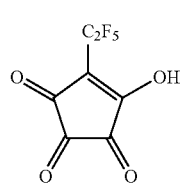 (a30)
-continued
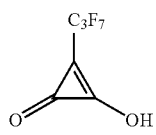 (a31)
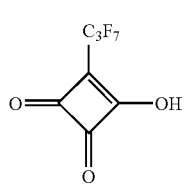 (a32)
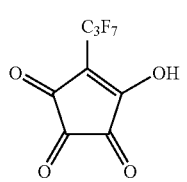 (a33)
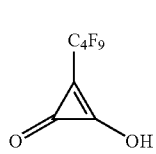 (a34)
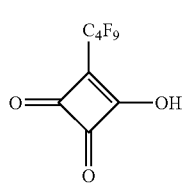 (a35)
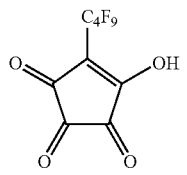 (a36)
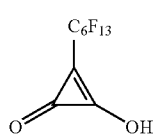 (a37)
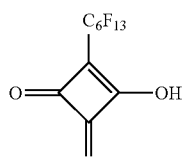 (a38)
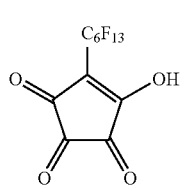 (a39)

(a40) 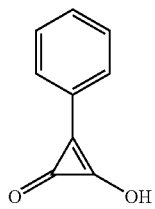
(a41) 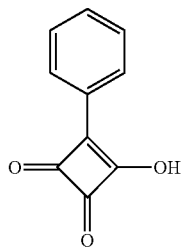
(a42) 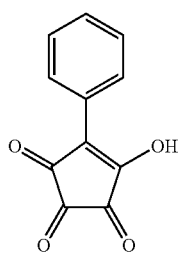
(a43) 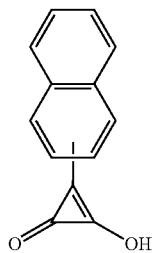
(a44) 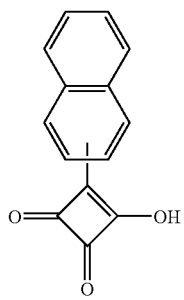
(a45) 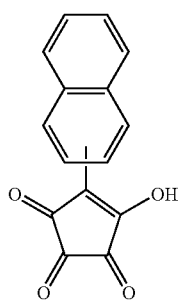
(a46) 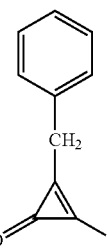
(a47) 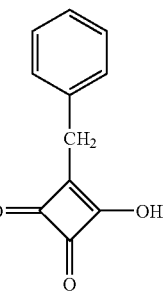
(a48) 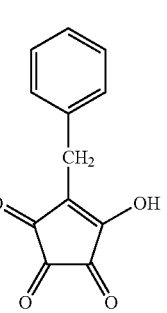
(a49) 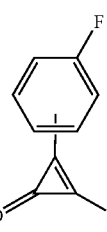
(a50) 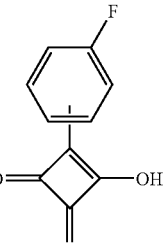
(a51) 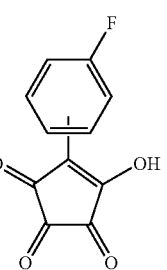

(a52) 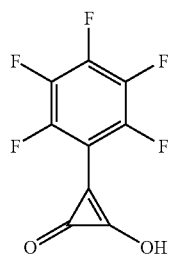
(a53) 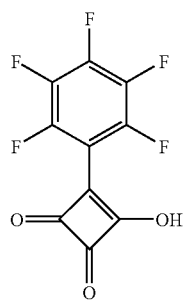
(a54) 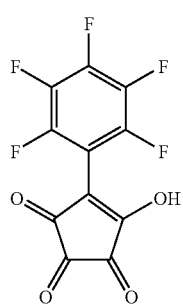
(a55) 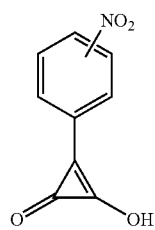
(a56) 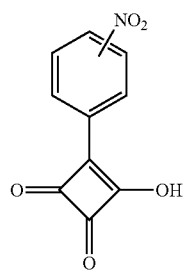
(a57) 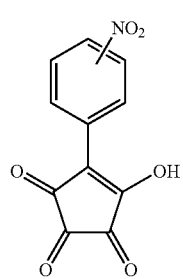
(a58) 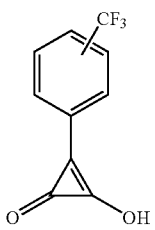
(a59) 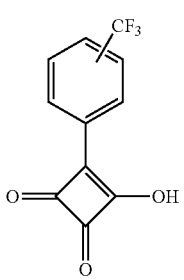
(a60) 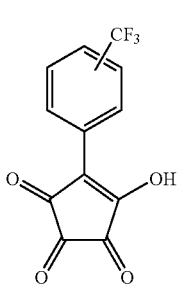
(a61) 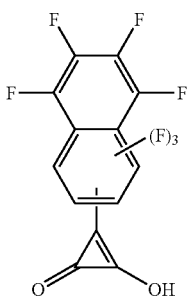
(a62) 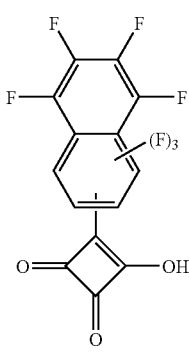

-continued
(a63)
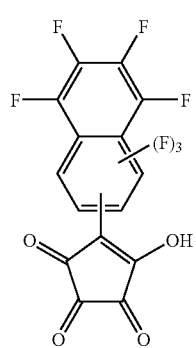
(a64)
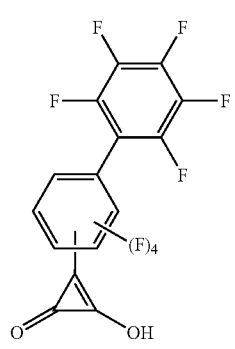
(a65)
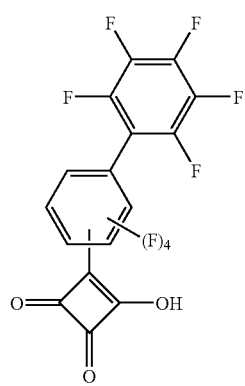
(a66)
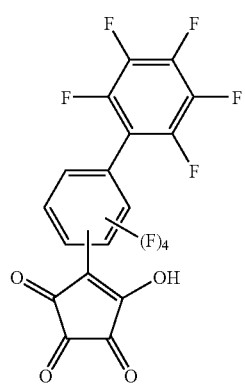
(b1)
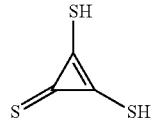
-continued
(b2)
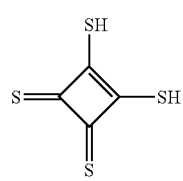
(b3)
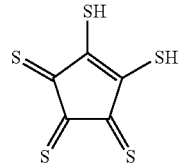
(b4)
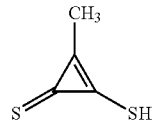
(b5)
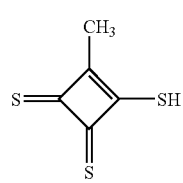
(b6)
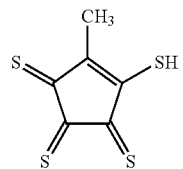
(b7)
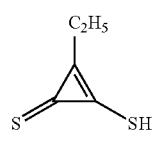
(b8)
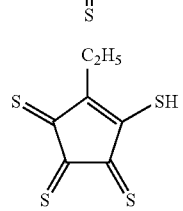
(b9)
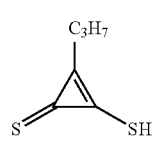
(b10)
(b11)

-continued
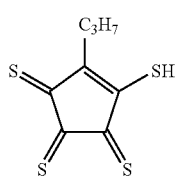
(b12)
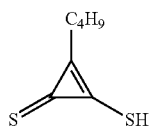
(b13)
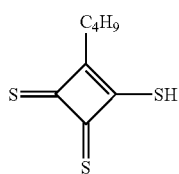
(b14)
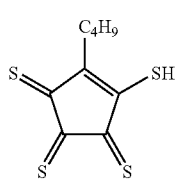
(b15)
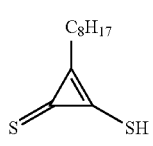
(b16)
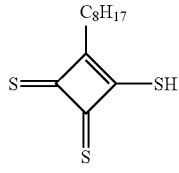
(b17)
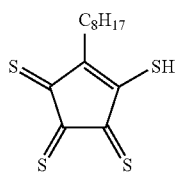
(b18)
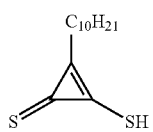
(b19)
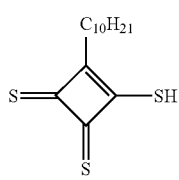
(b20)
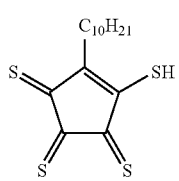
(b21)
-continued
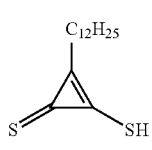
(b22)
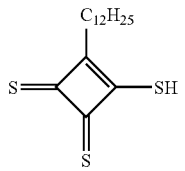
(b23)
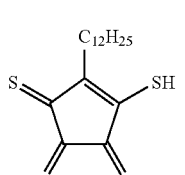
(b24)
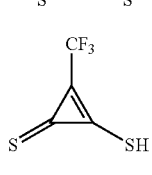
(b25)
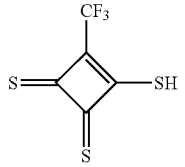
(b26)
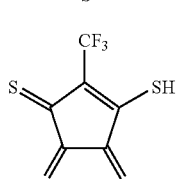
(b27)
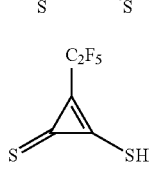
(b28)
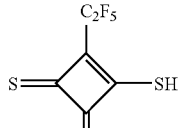
(b29)
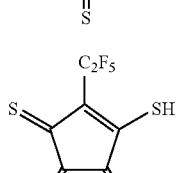
(b30)
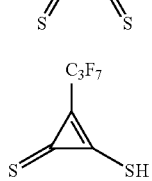
(b31)

(b32) 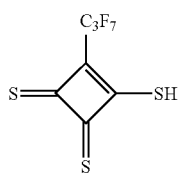
(b33) 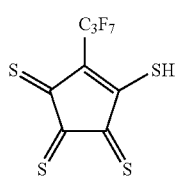
(b34) 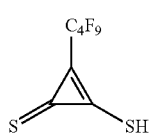
(b35) 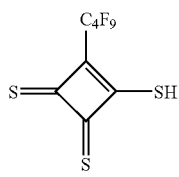
(b36) 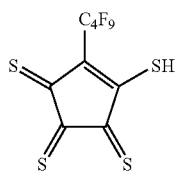
(b37) 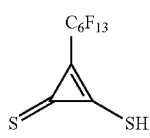
(b38) 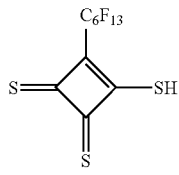
(b39) 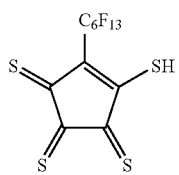
(b40) 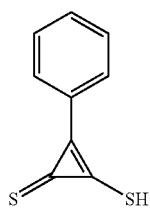
(b41) 
(b42) 
(b43) 
(b44) 
(b45) 
(b46)

(b47)
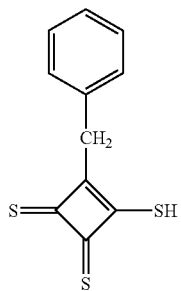
(b48)
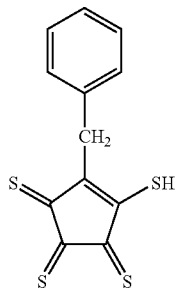
(b49)
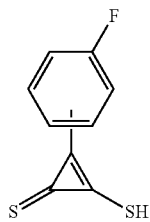
(b50)
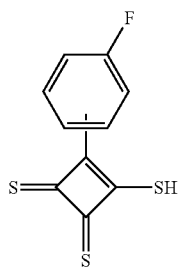
(b51)
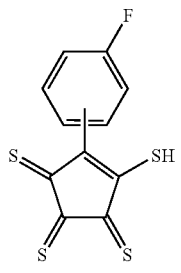
(b52)
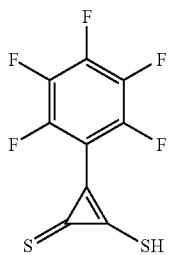
(b53)
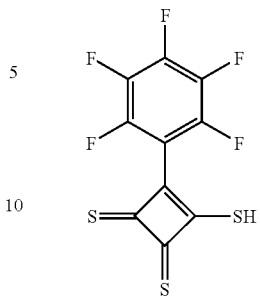
(b54)
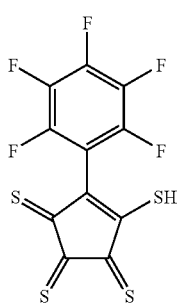
(b55)
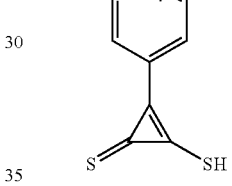
(b56)
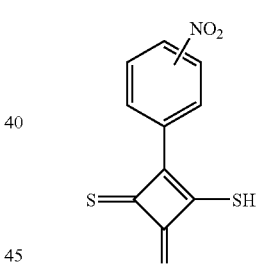
(b57)
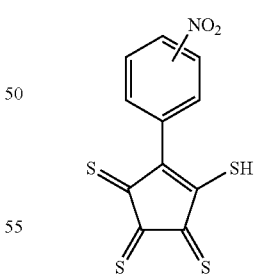
(b58)
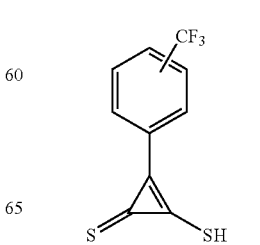

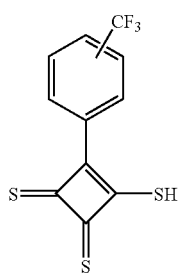
(b59)
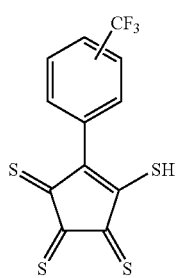
(b60)
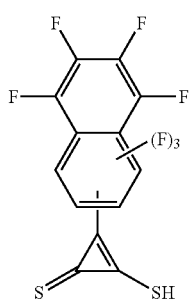
(b61)
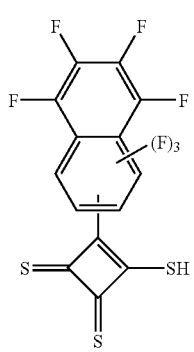
(b62)
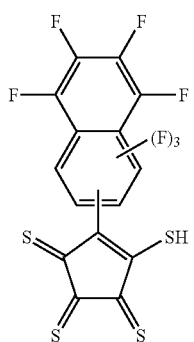
(b63)

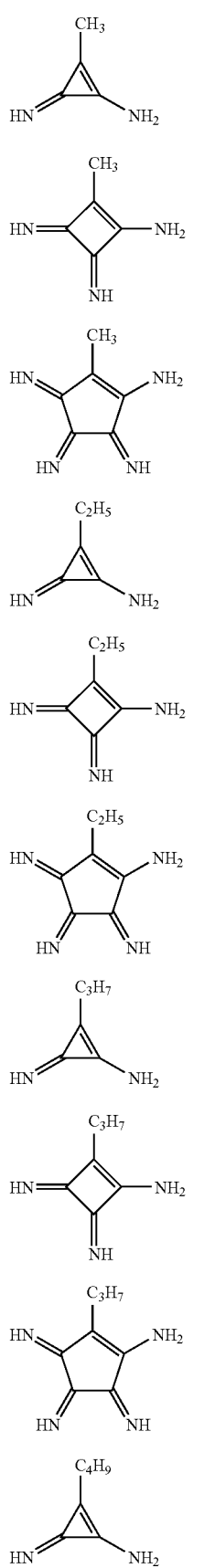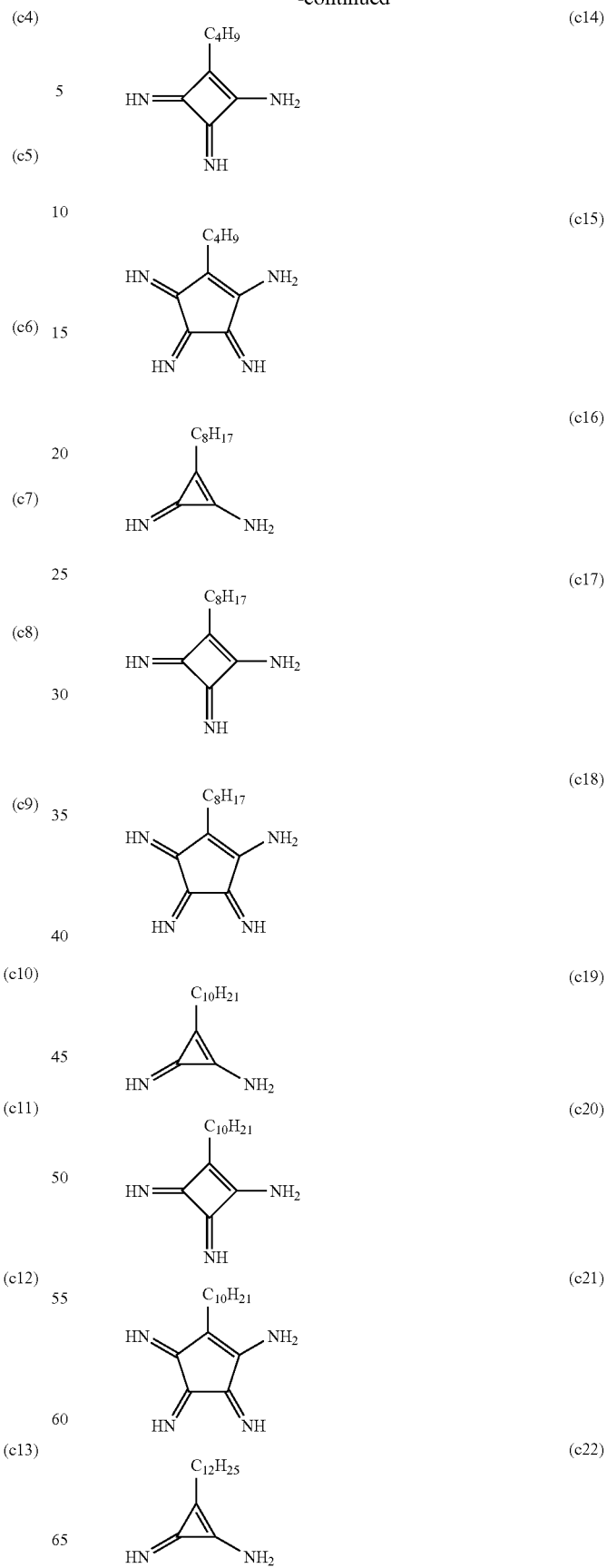

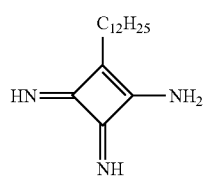 (c23)
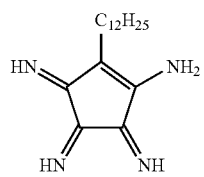 (c24)
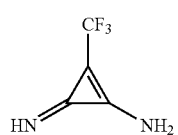 (c25)
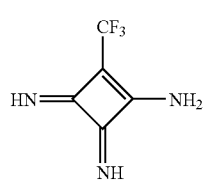 (c26)
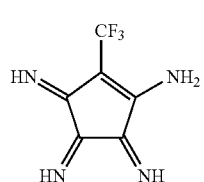 (c27)
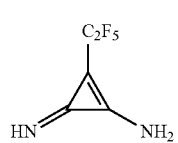 (c28)
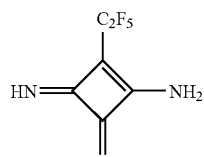 (c29)
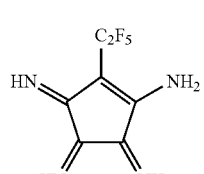 (c30)
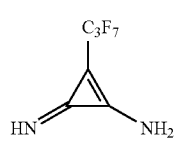 (c31)
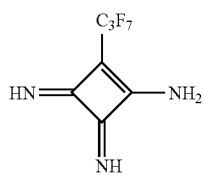 (c32)
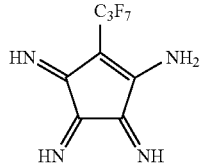 (c33)
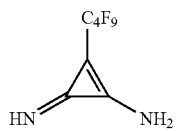 (c34)
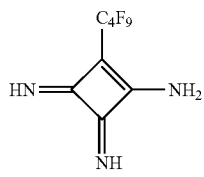 (c35)
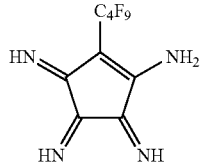 (c36)
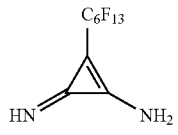 (c37)
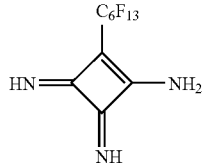 (c38)
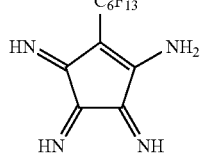 (c39)
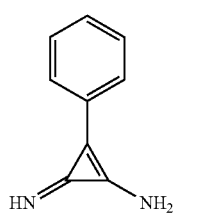 (c40)

(c41)
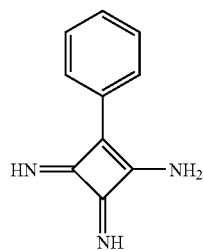
(c42)
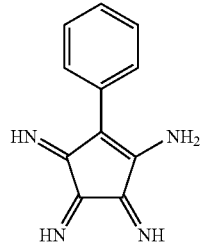
(c43)
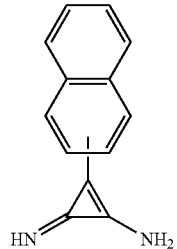
(c44)
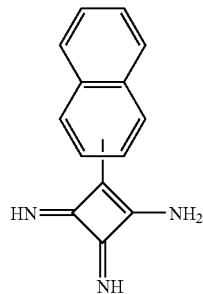
(c45)
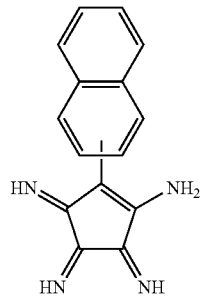
(c46)
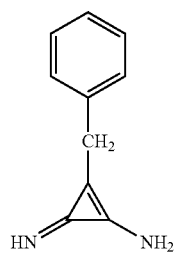
(c47)
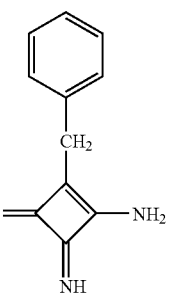
(c48)
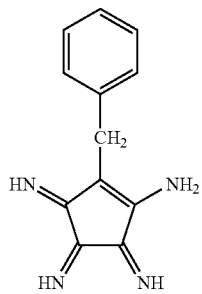
(c49)
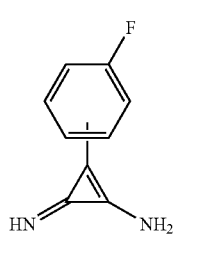
(c50)
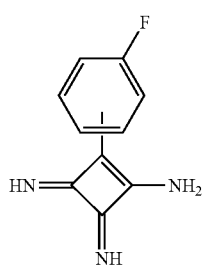
(c51)
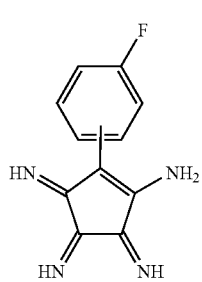
(c52)
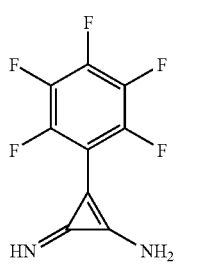

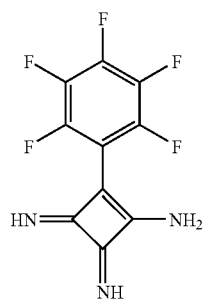 (c53)
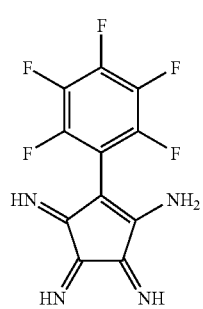 (c54)
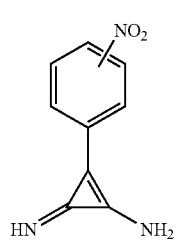 (c55)
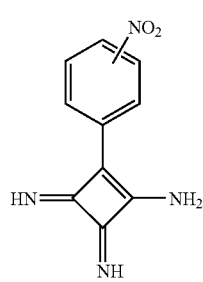 (c56)
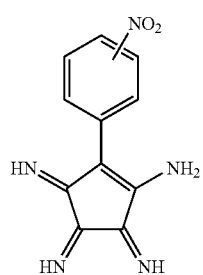 (c57)
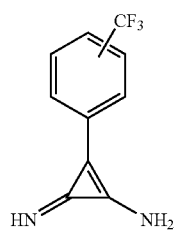 (c58)
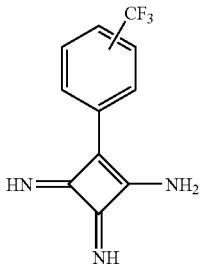 (c59)
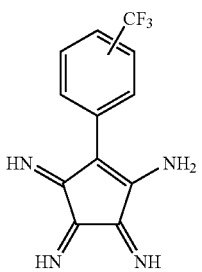 (c60)
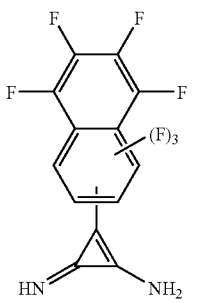 (c61)
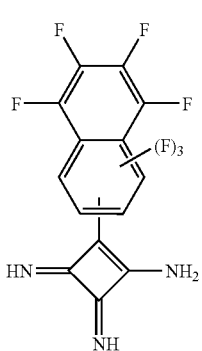 (c62)
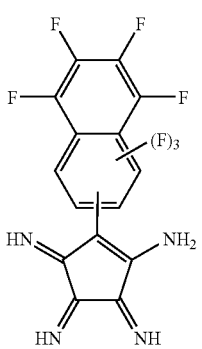 (c63)

-continued

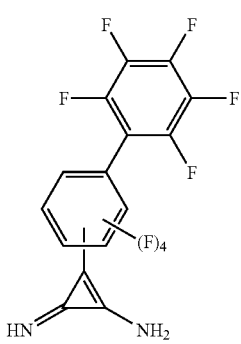

(c64)

(c65)

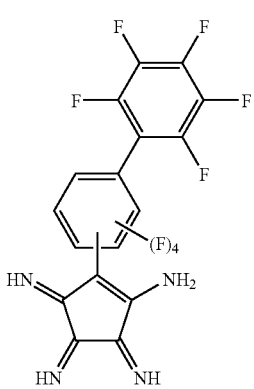

(c66)

In the present invention, the above-described oxocarbons are used. Among them, (a1) to (a66) are preferable, more preferable are (a2), (a5), (a8), (a11), (a14), (a17), (a20), (a23), (a26), (a29), (a32), (a35), (a38), (a41), (a44), (a47), (a50), (a53), (a56), (a59), (a62) and (a65), further preferable are (a2), (a5), (a17), (a26), (a29), (a41), (a44), (a50), (a53), (a59), (a62) and (a65), particularly preferable are (a2), (a41), (a51) and (a53).

Oxocarbons can be produced, for example, by the following methods. They may also be obtained from reagent manufactures.

(I) a method for producing a compound that R in oxocarbons (1) is alkyl or aryl using a lithium reagent (Journal of Organic Chemistry, 53, 2482, 2477 (1988)).

(II) a method for producing a compound that R in oxocarbons (1) is alkyl or aryl using a Grignard reagent (Heterocycles, 27(5), 1191 (1988)).

(III) a method for producing a compound that R in oxocarbons (1) is alkyl or aryl using a tin reagent (Journal of Organic Chemistry, 55, 5359 (1990), Tetrahydron Letters, 31(30), 4293 (1990)).

(IV) a method using Friedel Crafts reaction (Synthesis, p. 46 (1974)).

Various derivatives can be synthesized in accordance with these methods. When an ester was obtained by a method of (I) to (IV), the ester is hydrolyzed with acid or alkali to give oxocarbons that B in the general formula (1) is a hydrogen atom. When B in the general formula (1) is an alkali metal, oxocarbons that B is a hydrogen atom can be obtained by neutralization with a solution containing an alkali metal hydroxide. The formula (1) is expressed as a free acid form, and when a hydrogen atom expressed in the formula (1) was replaced with a monovalent metal ion, oxocarbons of free acid expressed in the formula (1) can be obtained by neutralization with a solution containing an alkali metal hydroxide.

The polymer composition of the present invention contains the above-described oxocarbon and a polymer.

Herein, as the polymer, for examples, there are listed vinyl polymers typified by polyvinyl pyrrolidones, poly(meth) acrylic acids, poly(meth)acrylates, poly(meth)acrylonitriles, polystyrenes, polyvinyl pyridines, polyethylenes, polypropylenes, polybutenes, polyvinylidene fluorides, polytetrafluoroethylenes, polyvinyl chlorides; polyoxyalkylenes, polysiloxanes, polyesters, polyimides, polyamides, polybenzoxazoles, polybenzimidazoles, polyarylene ethers, polyarylenes, polyarylene sulfides, polyetherketones, polyethersulfones, and polyphosphazene; a copolymer with repeating unit constituting these polymers and a mixture thereof.

Among them, preferable are polyvinyl pyrrolidones, poly (meth)acrylates, poly(meth)acrylonitriles, polystyrenes, polyvinyl pyridines, polyvinylidene fluorides, polytetrafluoroethylenes, polyesters, polyimides, polybenzoxazoles, polybenzimidazoles, polyarylene ethers, polyarylenes, polyetherketones, polyethersulfones, a copolymer thereof; and a mixture thereof, more preferable are polyvinyl pyrrolidones, polyesters, polyvinyl pyridines, polybenzimidazoles, polyethersulfones, a copolymer thereof and a mixture thereof.

Further, the molecular weight of the above-mentioned polymer is generally 1000 or more in number-average, and when it is used as a membrane form, it is preferably 5000 or more from the point of maintaining a shape as a membrane. The number-average molecular weight is generally about 2000000 or less, and when it is used as a membrane form, it is preferably about 1000000 or less from the point of forming into a membrane.

As other examples of the polymer used in the present invention, besides the above-described polymers, a polymer electrolyte is listed. The polymer electrolyte is not particularly limited as long as it can be used as an electrolyte. While there can be used a polymer electrolyte having an ion exchange group through a covalent bond, and a blend of an inorganic strong acid with a polymer, it is preferable to have an ion exchange group through a covalent bond.

As the ion exchange group, for example, there are listed a cation exchange group such as —SO$_3$H, —COOH, —PO (OH)$_2$, —POH(OH), —SO$_2$NHSO$_2$—, -Ph(OH) (Ph represents a phenylene group), an oxocarbon group expressed by the following general formula (2):

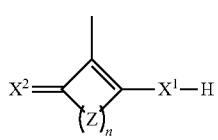

(2)

wherein X$^1$, X$^2$, Z and n represent the same meanings as in foregoing formula (1), and an anion exchange group such as —NH$_2$, —NHR, —NRR', —NRR'R''$^+$, —NH$_3^+$ (R represents an alkyl group, a cycloalkyl group, an aryl group etc.). A part of, or all of ion exchange groups may form a salt with the counter ion.

The ion exchange group is preferably a cation exchange group, further preferably —$SO_3H$, —$PO(OH)_2$, —POH (OH), —$SO_2NHSO_2$— and an oxocarbon group, particularly preferably —$SO_3H$, —$PO(OH)_2$, and an oxocarbon group, and most preferably —$SO_3H$.

Examples of the polymer electrolyte include, for example, (A) a polymer electrolyte which is a polymer composed of an aliphatic hydrocarbon as its main chain being introduced an ion exchange group into; (B) a polymer electrolyte which is a polymer composed of an aliphatic hydrocarbon that a part of, or whole of hydrogen atoms in its main chain is replaced with fluorine being introduced an ion exchange group into; (C) a polymer electrolyte which is a polymer having an aromatic ring in its main chain being introduced an ion exchange group into; (D) a polymer electrolyte which is a polymer composed of an inorganic substance having substantially no carbon atom in its main chain being introduced an ion exchange group into; (E) a polymer electrolyte having a nitrogen atom in its main chain or side chain being introduced an acidic compound into, through ion bonding; and (F) a polymer electrolyte composed of a mixture of (A) to (E); and an electrolyte that an ion exchange group is introduced into a copolymer with repeating units constituting: (A') a polymer composed of an aliphatic hydrocarbon as its main chain; (B') a polymer composed of an aliphatic hydrocarbon that a part of, or whole of hydrogen atoms in its main chain is replaced with fluorine; (C') a polymer having an aromatic ring in its main chain; (D') a polymer composed of an inorganic substance having substantially no carbon atom in its main chain; and (E') a polymer having a nitrogen atom in its main chain or side chain. Additionally, when an ion exchange group is introduced into a copolymer with repeating unit constituting a polymer having a nitrogen atom in its main chain or side chain, an acidic compound may be introduced through ion bonding in the same manner as aforementioned.

As the polymer electrolyte mentioned in (A), for example, there are listed polyvinyl sulfonic acid, polystyrene sulfonic acid and poly(a-methylstyrene) sulfonic acid.

Further, as the polymer electrolyte mentioned in (B), there are listed a polymer, as typified by Nafion (trademark of Du Pont Corporation, same below), which has perfluoroalkyl sulfonic acid in the side chain, and the main chain is perfluoroalkane; sulfonic acid type polystyrene-graft-ethylene-tetrafluoroethylene copolymer composed of a main chain formed by copolymerizing carbon fluoride type vinyl monomer with carbon hydride type vinyl monomer, and a hydrocarbon type side chain having a sulfonic acid group (ETFE: e.g. Japanese Patent Application 9-102322 (1997)); and sulfonic acid type poly(trifluorostyrene)-graft-ETFE membrane that a,β,β-trifluorostyrene is subjected to a graft polymerization into a membrane formed by copolymerizing carbon fluoride type vinyl monomer with carbon hydride type vinyl monomer, and a sulfonic acid group is introduced therein to give a solid polymer polymer electrolyte membrane (e.g. U.S. Pat. Nos. 4,012,303 and 4,605,685).

As the polymer electrolyte mentioned in (C), its main chain may be interrupted by a hetero atom such as an oxygen atom, for example, there are listed those that an ion exchange group is introduced into each of the polymers such as polyetheretherketone, polysulfone, polyethersulfone, poly(arylene ether), polyimide, poly((4-phenoxybenzoyl)-1,4-phenylene), polyphenylene sulfide, and polyphenylquinoxalene; and sulfoarylated polybenzimidazole, sulfoalkylated polybenzimidazole, phosphoalkylated polybenzimidazole (e.g. Japanese Patent Application Hei 9-110982 (1997)), and phosphonated poly(phenylene ether) (e.g. J. Appl. Polym. Sci., 18, 1969 (1974)).

As the polymer electrolyte mentioned in (D), for example, there are listed one that an ion exchange group is introduced into polyphophazene, and polysiloxane having a phosphonic acid group described in Polymer Prep., 41, no. 1, 70 (2000).

As the polymer electrolyte mentioned in (E), for example, listed is polybenzimidazole containing phosphoric acid described in Tokuhyo Hei 11-503262 (1999; published Japanese translation of PCT international publication for patent application).

As the polymer electrolyte that an ion exchange group is introduced into a copolymer with repeating units constituting the above-described (A') to (E'), there may be one that an ion exchange group is introduced into a random copolymer, an ion exchange group is introduced into an alternating copolymer, or an ion exchange group is introduced into a block copolymer. As the one that an ion exchange group is introduced into a random copolymer, for example, polymer electrolyte described in Japanese Patent Application Hei 10-021943 (1998) is listed. As for a block copolymer, a specific example of the block copolymer having a sulfonic acid group includes, for example, polymer electrolyte described in Japanese Patent Application 2001-250567.

The weight-average molecular weight of the above-described polymer electrolyte is generally 1000 or more, and when it is used as a membrane form, it is preferably 5000 or more from the point of maintaining a shape as a membrane.

The weight-average molecular weight is generally about 1000000 or less, and when it is used as a membrane form, it is preferably about 200000 or less from the point of forming into a membrane.

Further, when a polymer electrolyte is used, among the above-described polymer electrolyte of (A) to (E), polymer electrolyte of (C) which is a polymer having an aromatic ring in the main chain and a sulfonic acid group and/or a phosphonic acid group are introduced therein is preferably used.

While the distribution of ion exchange groups introduced in a polymer electrolyte is not particularly limited, preferable is a polymer electrolyte composed of a segment having an ion exchange group and a segment having substantially no ion exchange group.

The composition of the present invention containing the above-described polymer and oxocarbons has preferably 0.05 to 8 mmol/g of [amount of substance of oxocarbons (mmol)]/ [weight (g) of polymer+weight (g) of oxocarbons], i.e. an equivalent amount of oxocarbon in the composition, further preferably 0.1 to 7 mmol/g, particularly preferably 0.3 to 6 mmol/g, and most preferably 0.5 to 5 mmol/g.

Herein, when the equivalent amount of oxocarbons in the composition is 0.05 mmol/g or more, it is preferable because ion conductivity tends to increase, when 8 mmol/g or less, it tends to be preferable in water resistance.

Oxocarbons are generally used such that the equivalent amount of oxocarbons in the composition is in the range described above. The quantitative determination of the equivalent amount of oxocarbons in the composition of the present invention is obtained using a NMR method.

The polymer composition of the present invention is characterized by containing a polymer and an oxocarbon, the production method is not particularly limited; for example, there are listed a method that a polymer and an oxocarbon are dissolved, dispersed, or suspended in a solvent to mix, then, the solvent is removed; and a method that a polymer is synthesized under the presence of oxocarbon.

In this case, as a solvent in the former method, for example, there may be suitably selected from water, alcohol solvent, ketone solvent, ether solvent, halogenated solvent, sulfoxide solvent, sulfone solvent, amide solvent, aliphatic hydrocarbon solvent, aromatic hydrocarbon solvent, and a mixed solvent thereof.

Alcohol solvent includes methanol, ethanol, isopropanol and butanol; ketone solvent includes acetone, methyl isobutyl ketone, methyl ethyl ketone and benzophenone. Ether solvent includes diethyl ether, dibutyl ether, diphenyl ether, tetrahydrofuran (hereinafter abbreviated as THF), dioxane, dioxolan, ethyleneglycol monomethyl ether, ethyleneglycol monoethyl ether, propyleneglycol monomethyl ether, and propyleneglycol monoethyl ether.

Haloganated solvent includes chloroform, dichloromethane, 1,2-dichloroethane, 1,1,2,2-tetrachloroethane, chlorobenzene and dichlorobenzene; sulfoxide solvent includes dimethyl sulfoxide (hereinafter abbreviated as DMSO). Sulfone solvent includes diphenylsulfone and sulfolane; amide solvent includes N,N-dimethylacetoamide (hereinafter abbreviated as DMAC), N-methylacetoamide, N,N-dimethylformamide (hereinafter abbreviated as DMF), N-methylformamide, formamide and N-methylpyrrolidone (hereinafter abbreviated as NMP). Aliphatic hydrocarbon solvent includes pentane, hexane, heptane and octane; aromatic hydrocarbon solvent includes benzene, toluene and xylene.

Among them, it is preferable to select from alcohol solvent, ether solvent, halogenated solvent, amide solvent and a mixed solvent thereof. It is further preferable to select from water, methanol, THF, dichloromethane, DMAc and a mixed solvent thereof.

As a method to remove solvents, a method that solvents in a mixed solution, dispersion or suspension are removed by evaporation is listed, and it can be also possible to form a membrane by using a solvent-casting method described later.

Further, as a method to obtain a polymer composition by synthesizing a polymer under the presence of oxocarbons, as the known methods under the presence of oxocarbons, for example, there are listed the synthesis of polymer using a radical polymerization, cation polymerization, anion polymerization, ion polymerization using a Zieglar-Natta catalyst, ring-opening polymerization, elimination polymerization, polyaddition, polycondensation, addition condensation ("Experimental methods for synthesis of polymer", p. 125-357 (1972), published by Kagaku-Dojin Publishing Company, INC) and also the methods to obtain polymer compositions. Additionally, in the case of a possible side reaction for oxocarbons to disturb polymerization in a polymerization reaction, for example, when an anion reaction is carried out under the presence of oxocarbons having a hydroxyl group, the hydroxyl group can be protected for use by the known protection method of protecting with an alkoxy group, siloxy group or ester group. In this case, a target material can be obtained by eliminating the protection group after polymerization by the known method.

Next, the polymer composition of the present invention will be described in a case where it is used as a separating membrane of an electrochemical device such as fuel cells.

In this case, the polymer composition of the present invention is generally used in a film shape. The method for converting it into a film is not particularly limited; for example, a film forming method from a solution state (solvent casting method) is preferably used.

Specifically, a polymer composition is dissolved in a suitable solvent, the resultant solution is applied on a glass plate, and the solvent is removed, thereby to conduct a film forming. The solvent used in film forming is not particularly limited as long as it can dissolve the polymer composition and can be removed afterward, and there are preferably used aprotic polar solvents such as DMF, DMAc, NMP and DMSO; or chlorinated solvents such as dichloromethane, chloroform, 1,2-dichloroethane, chlorobenzene and dichlorobenzene; alcohols such as methanol, ethanol and propanol; alkyleneglycol monomethyl ethers such as ethyleneglycol monomethyl ether, ethyleneglycol monoetyl ether, propyleneglycol monomethyl ether and propyleneglycol monoethyl ether; and ether solvents such as THF, 1,3-dioxolan, 1,4-dioxane, 1,3-dioxane, tetrahydropyran, dibutyl ether, tert-butyl methyl ether, diphenyl ether and crown ethers. These may be used alone, or may be used in a mixture of 2 kinds or more of solvents according to need.

Above all, preferable are DMSO, DMF, DMAc, NMP, THF and 1,3-dioxolan because they have high solubility for the polymer composition.

The thickness of film is not particularly limited, and is preferably 10 to 300 μm, and particularly preferably 20 to 100 μm. A film with 10 μm or thinner sometimes does not have sufficient practical strength, whereas a film with thickness of thicker than 300 μm becomes high in membrane resistance, which tends to lower the characteristics of electrochemical devices. The membrane thickness can be controlled by the concentration of solution and coating thickness on a substrate.

Moreover, in order to improve various properties of film, it is possible for the polymer composition of the present invention to contain a plasticizer, stabilizer and mold release agent used for general polymer compounds. Other polymer can also be compounded/alloyed with the polymer composition of the present invention by a method of blend-casting in the same solvent.

In order to make water-control easier in fuel cell applications, it is also known that inorganic or organic fine particles are added as a water holding agent. Any of these known methods can be used as long as it does not disturb the object of the present invention.

Further, to improve the mechanical strength of film, a film can be crosslinked by irradiation of electron/radioactive ray (e.g. Japanese Patent Application Hei 11-111310 (1999)). Further, there are known a method that a film is immersed/combined with a porous film or sheet (Japanese Patent Application Hei 6-29032 (1994)), and a method that fibers and pulp are mixed to reinforce a film, any of these known methods can be used as long as it does not disturb the object of the present invention.

The battery of the present invention is characterized by having at least one polymer electrolyte or polymer electrolyte membrane described above of the present invention. Herein, as the battery, fuel cells and a lithium ion secondary battery are listed, and in particular, fuel cells are preferable; among fuel cells, a solid polymer type fuel cell is most preferable.

Next, the fuel cell of the present invention will be described.

The fuel cell of the present invention is characterized by having at least one polymer electrolyte or polymer electrolyte membrane described above of the present invention.

The fuel cell of the present invention can be produced by jointing an electrically conductive substance as a catalyst and power collector onto both faces of a film.

The catalyst is not particularly limited as long as it can activate oxidation-reduction reaction with oxygen or hydrogen, can use the known one, but it is preferable to use a fine particle of platinum. The fine particle of platinum is often carried on particulate or fibrous carbon such as active carbon and graphite, and preferably used.

The electrically conductive substance as a power collector can also use the known material, but porous carbon fabric, carbon non-woven fabric or carbon paper is preferable because of effective transportation of raw gas to a catalyst.

Regarding a method for jointing platinum fine particles or carbon carrying platinum fine particles onto porous carbon fabric or carbon paper and a method for jointing it on a polymer electrolyte film, for example, there can be used the known method described in J. Electrochem. Soc.: Electrochemical Science and Technology, 1988, 135(9), 2209.

The polymer composition of the present invention can also be used as a proton conductive material which is one component of a catalyst composition constituting a catalyst layer of solid polymer type fuel cell.

The thus produced fuel cell of the present invention can be used in various types using fuels such as hydrogen gas, reformed hydrogen gas, methanol and dimethyl ether.

Next, the oxocarbon compound of the present invention will be described.

The oxocarbon compound of the present invention is a compound expressed by the foregoing formula (1), and it is an oxocarbon compound characterized in that R is a halogeno substituted aryl group.

As described above, the polymer composition containing the oxocarbon compound and a polymer compound can be preferably used for an electrolyte membrane of fuel cell because of excellent proton conductivity.

As the oxocarbon compound of the present invention, a compound that the halogeno substituted aryl group is selected from the group consisting of the following formulas (2a) to (2c) is listed:

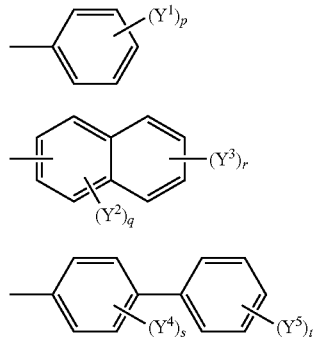

wherein p represents an integer of 1 to 5, q represents an integer of 0 (inclusive) to 3, r represents an integer of 0 (inclusive) to 4, and a value of (q+r) is 1 to 7, s represents an integer of 0 (inclusive) to 4, t represents an integer of 0 (inclusive) to 5, and a value of (s+t) is 1 to 9; $Y^1$ to $Y^5$ each independently represents a halogeno group, when $Y^1$ to $Y^5$ are each plural, these may be same or different.

Regarding the halogeno aryl group, it is preferable that the halogeno group is a fluoro group. For such compounds, specifically there are listed the aforementioned (a49) to (a54), (a58) to (a66), (b49) to (b54), (b58) to (b66), (c49) to (c54), and (c58) to (c66).

As the oxocarbon compound of the present invention, it is preferable that a halogeno aryl group is the above-described (2a) because of high proton conductivity. Above all, the aforementioned (a49) to (a54), (b49) to (b54), and (c49) to (c54) are preferred. Among them, (a49) to (a54) are further preferable, (a50) and (a53) are particularly preferable.

Regarding the oxocarbon compound of the present invention, as a specific structure formula, of the compounds expressed as (a50), there is listed an oxocarbon compound expressed by the following formula (3) where a para position of an oxocarbon group is substituted with fluorine:

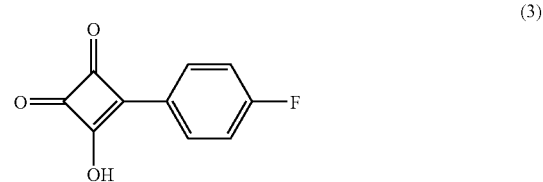

Further, regarding the oxocarbon compound of the present invention, as a specific structure formula, there is listed an oxocarbon compound of (a53) expressed by the following formula (4):

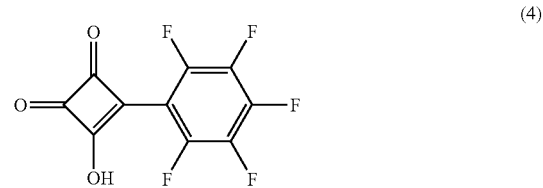

The above compounds are listed as oxocarbon compounds that R is a halogeno substituted aryl group, and these may be in a free acid form having a property of proton acid, or free acid may be replaced with a monovalent metal atom to be a neutralized form. The monovalent metal atom includes a lithium atom, sodium atom, potassium atom, cesium atom, and silver atom. B is preferably a hydrogen atom, lithium atom, sodium atom, potassium atom and cesium atom, further preferably a lithium atom, sodium atom, and potassium atom, further more preferably a hydrogen atom and a lithium atom, and particularly preferably a hydrogen atom.

In the case where the compound of the present invention is used as an electrolyte for a lithium secondary battery, lithium is used as B. In the case where the compound of the present invention is used in a solid polymer type fuel cell, it is preferable when substantially all functional groups are in a free acid form.

In the above description, embodiments of the present invention have been explained, but the above-disclosed embodiments of the present invention are mere illustration, the scope of the present invention is not limited to these embodiments. The scope of the present invention is shown in claims, further includes all modifications within being equivalent to the spirit and scope described in claims.

While the present invention will be described in detail with reference to Examples below, the present invention is not to be limited to these examples.

Ion exchange capacity was measured by a titration method.

Proton conductivity (s) was measured in the following way.

On the surface of a strip-like membrane sample with 1.0 cm width, platinum plates (width: 5.0 mm) were pressed at intervals of 1.0 cm, the sample was held in a chamber with constant temperature and humidity, alternating current impedance was measured at $10^6$ to $10^{-1}$ Hz across the platinum plates, and obtained by the following formula:

$$s(S/cm)=1/(R \times d)$$

wherein on Cole-Cole plot, when an imaginary component of complex impedance is zero, an actual component of complex impedance is defined as R(O), d represents membrane thickness (cm).

Tensile test was measured in accordance with Japanese Industrial Standards (JIS K 7127) at 23° C. and 50% of relative humidity at a test speed of 10 mm/min.

REFERENCE EXAMPLE 1

Synthesis of
3-Hydroxy-4-phenylcyclobut-3-ene-1,2-dione
(Compound II)

In accordance with a method described in Journal of Organic Chemistry, 1988, 53(11), 2482, 3-(1-Methylethoxy)-4-Phenylcyclobut-3-ene-1,2-dione was produced. Then, a 100 ml flask was charged with 0.63 g thereof, 12 ml of THF and 36 ml of 12N hydrochloric acid, and stirred at 100° C. for 5 hours. Thereafter, the resultant mixture was allowed to stand to room temperature, a water layer was washed with chloroform, the water layer was condensed, thereby to give 0.24 g of 3-Hydroxy-4-phenylcyclobut-3-ene-1,2-dione (compound II). The structure was confirmed by $^1H$ NMR and $^{13}C$ NMR.

REFERENCE EXAMPLE 2

Synthesis of 4-(4-fluorophenyl)-3-Hydroxy-cyclobut-3-ene-1,2-dione (Compound V)

In accordance with a method described in Journal of Organic Chemistry, 1990, 55, 5359, 4-(1-Methylethoxy)-3-(tri-n-butylstannyl)cyclobut-3-ene-1,2-dione (compound III) was produced.

Next, to a flask substituted with inert gas, were added 92.0 mg (0.49 mmol) of copper (I) iodide, 1.17 g (5.24 mmol) of p-fluoroiodobenzene and 0.22 g (0.29 mmol) of $[(C_6H_5)_3P]_2Pd(CH_2C_6H_5)Cl$, the mixture was dissolved in 0.6 ml of DMF, then, 2.00 g (4.8 mmol) of the compound III obtained above was added dropwise thereto. After stirring for 4 hours, the reaction liquid was diluted with 50 ml of diethyl ether, washed once with 50 ml of saturated aqueous ammonium chloride solution, and washed three times with 50 ml of 10 wt % potassium fluoride aqueous solution. Ether and DMF were distilled away, the resultant crude product was purified by a column chromatography with silica gel as a filler and hexane:ether=3:1 (vol/vol) as a developing solvent, thereby to give 0.55 g of 4-(4-fluorophenyl)-3-(1-Methylethoxy)-cyclobut-3-ene-1,2-di one (compound IV).

Next, 0.37 g (1.58 mmol) of compound IV was dissolved in 0.1 ml of THF, 7.0 ml of 12N hydrochloric acid was added thereto, and stirred for 3 hours. Then, 10 ml of water was added to the reaction liquid to dilute, and washed once with 10 ml of $CH_2Cl_2$. Water in a water layer was distilled away, thereby to give 0.179 g of 4-(4-fluorophenyl)-3-Hydroxy-cyclobut-3-ene-1,2-dione (compound V). The structure was confirmed by $^1H$ NMR ($D_2O$ solvent, 7.21 ppm (2H), 7.96 ppm (2H)) and $^{19}F$ NMR ($D_2O$ solvent, −109.0 ppm). The purity was measured by HPLC to confirm 99% or more (area ratio of peak).

REFERENCE EXAMPLE 3

Production of 3-Hydroxy-4-(2,3,4,5,6-pentafluorophenyl)-cyclobut-3-ene-1, 2-dione (Compound VII) and Composition To a flask substituted with inert gas, were added 18.0 mg (0.095 mmol) of copper (I) iodide, 0.30 g (1.00 mmol) of pentafluoroiodobenzene and 43.0 mg (0.057 mmol) of $[(C_6H_5)_3P]_2Pd(CH_2C_6H_5)Cl$, the mixture was dissolved in 1.0 ml of DMF, then, 0.40 g (0.93 mmol) of the compound III was added dropwise thereto. After stirring for 4 hours, the reaction liquid was diluted with 50 ml of diethyl ether, washed once with 50 ml of saturated aqueous ammonium chloride solution, and washed three times with 50 ml of 10 wt % potassium fluoride aqueous solution. Ether and DMF were distilled away, the resultant crude product was purified by a column chromatography with silica gel as a filler and hexane:ether=3:1 (vol/vol) as a developing solvent, thereby to give 0.53 g of 4-(2,3,4,5,6-prentafluorophenyl)-3-(1-Methylethoxy)-cyclobu t-3-ene-1,2-dione (compound VI).

Next, 0.053 g (0.173 mmol) of compound VI was dissolved in 0.1 ml of THF, 1.5 ml of 12N hydrochloric acid was added thereto, and stirred for 3 hours. Then, 10 ml of water was added to the reaction liquid to dilute, and washed once with 10 ml of $CH_2Cl_2$. Water in a water layer was distilled away, thereby to give 23 mg of 3-Hydroxy-4-(2,3,4,5,6-pentafluorophenyl)-cyclobut-3-ene-1, 2-dione (compound VII). The structure was confirmed by $^{19}F$ NMR ($D_2O$ solvent, KF standard (−125.3 ppm), chemical shift value: −138.3 ppm, −156.2 ppm −165.7 ppm). No peak was observed by $^1H$ NMR. The purity was measured by HPLC to confirm 99% or more (area ratio of peak).

EXAMPLE 1

A 50 ml flask was charged with 0.50 g of poly(N-vinylpyrrolidone) (manufactured by Aldrich Corporation, hereinafter abbreviated as PVP), 0.20 g (1.75 mmol, manufacture by Tokyo Chemical Industry Co., Ltd.) of 3,4-dihydroxy-3-cyclobutene-1,2-dione (hereinafter abbreviated as compound I) and 5.0 ml of ion-exchanged water, stirred at room temperature for 30 minutes to obtain a uniform solution. This solution was spread on a petri dish, and water was distilled away at 80° C., thereby to give a membrane A of 85 μm thickness. The value of [amount of substance of oxocarbons (mmol)]/[weight (g) of polymer compound+weight (g) of oxocarbons] of membrane A was 2.51 (mmol/g). The proton conductivity of membrane A is shown in Table 1.

EXAMPLE 2

A 50 ml flask was charged with 0.38 g of polyethersulfone (Sumika Excel 5003P manufactured by Sumitomo Chemical Co., Ltd. hereinafter abbreviated as PES) and 0.15 g (0.86 mmol) of compound II, 3 ml of DMAc was added thereto, dissolved to obtain a uniform solution. This solution was cast on a glass plate, dried at 80° C. in an oven, thereby to give a uniform membrane B of 180 μm thickness. The value of [amount of substance of oxocarbons (mmol)]/[weight (g) of polymer compound+weight (g) of oxocarbons] of membrane B was 1.63 (mmol/g). The measurement result on the proton conductivity of membrane B is shown in Table 2.

EXAMPLE 3

A uniform membrane C of 140 μm thickness was obtained in the same manner as in Example 2 except that 0.28 g of PES and 0.22 g (1.26 mmol) of compound II were used. The value of [amount of substance of oxocarbons (mmol)]/[weight (g) of polymer compound+weight (g) of oxocarbons] of membrane C was 2.53 (mmol/g). The measurement result on the proton conductivity of membrane C is shown in Table 2.

EXAMPLE 4

A uniform membrane D of 175 μm thickness was obtained in the same manner as in Example 2 except that 0.28 g of polysulfone (manufactured by Aldrich Corporation) was used in place of PES. The value of [amount of substance of oxocarbons (mmol)]/[weight (g) of polymer compound+weight (g) of oxocarbons] of membrane D was 2.00 (mmol/g). The measurement result on the proton conductivity of membrane D is shown in Table 2.

COMPARATIVE EXAMPLE 1

In accordance with a method described in example 1 of Japanese Patent Application Hei 10-21943 (1998), a polymer electrolyte a was obtained by polycondensation of 4,4'-dihydroxydiphenylsulfone, 4,4'-dihydroxybiphenyl and 4,4'-dichlorodiphenylsulfone, then by sulfonation of the resultant polycondensate. The equivalent amount of sulfonic acid group in the polymer was 1.1 mmol/g.

Next, the polymer electrolyte a was dissolved in DMAc to obtain a uniform solution, the solution was spread on a petri dish, and DMAc was distilled away at 80° C., thereby to give a membrane E of 35 μm thickness. The proton conductivity of membrane E is shown in Table 1 and Table 2.

EXAMPLE 5

A container of 20 ml inner volume was charged with 41.0 mg of PVP, 17.7 mg (0.092 mmol) of compound V and 3.0 ml of ion-exchanged water, stirred at room temperature for 30 minutes to obtain a uniform solution. This solution was spread on a petri dish, and water was distilled away at 80° C., thereby to give a membrane F of 145 μm thickness. The value of [amount of substance of oxocarbons (mmol)]/[weight (g) of polymer compound+weight (g) of oxocarbons] of membrane F was 1.57 (mmol/g). The proton conductivity of membrane F is shown in Table 1.

EXAMPLE 6

A container of 20 ml inner volume was charged with 32.5 mg of PVP, 23.0 mg (0.0871 mmol) of compound VII and 3.0 ml of ion-exchanged water, stirred at room temperature for 30 minutes to obtain a uniform solution. This solution was spread on a petri dish, and water was distilled away at 80° C., thereby to give a membrane G of 158 μm thickness. The value of [amount of substance of oxocarbons (mmol)]/[weight (g) of polymer compound+weight (g) of oxocarbons] of membrane G was 1.57 (mmol/g). The proton conductivity of membrane G is shown in Table 1.

EXAMPLE 7

A flask is charged with compound VIII that $X^1$, $X^2$, Z, n and R in the formula (1) are shown in Table 4, polybenzimidazole and NMP, stirred to obtain a uniform solution. This solution is spread on a petri dish, solvent is evaporated for drying to give a membrane H of composition. In this case, when compound VIII and polybenzimidazole are chosen so that [amount of substance of oxocarbons (mmol)]/[weight (g) of polymer electrolyte+weight (g) of oxocarbons] of membrane H is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

EXAMPLE 8

A flask is charged with compound IX that $X^1$, $X^2$, Z, n and R in the formula (1) are shown in Table 4, polybenzimidazole and NMP, stirred to obtain a uniform solution. This solution is spread on a petri dish, solvent is evaporated for drying to give a membrane I of composition. In this case, when compound Ix and polybenzimidazole are chosen so that [amount of substance of oxocarbons (mmol)]/[weight (g) of polymer electrolyte+weight (g) of oxocarbons] of membrane I is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

EXAMPLE 9

A flask is charged with compound X that $X^1$, $X^2$, Z, n and R in the formula (1) are shown in Table 4, PVP and water, stirred to obtain a uniform solution. This solution is spread on a petri dish, solvent is evaporated for drying to give a membrane J of composition. In this case, when compound X and PVP are chosen so that [amount of substance of oxocarbons (mmol)]/[weight (g) of polymer electrolyte+weight (g) of oxocarbons] of membrane J is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

EXAMPLE 10

A flask is charged with compound $X^1$ that $X^1$, $X^2$, Z, n and R in the formula (1) are shown in Table 4, PVP and water, stirred to obtain a uniform solution. This solution is spread on a petri dish, solvent is evaporated for drying to give a membrane K of composition. In this case, when compound $X^1$ and PVP are chosen so that [amount of substance of oxocarbons (mmol)]/[weight (g) of polymer electrolyte+weight (g) of oxocarbons] of membrane K is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

EXAMPLE 11

A flask is charged with compound XII that $X^1$, $X^2$, Z, n and R in the formula (1) are shown in Table 4, PES and a mixed liquid of methylene chloride:methanol=9:1 (vol/vol), stirred to obtain a uniform solution. This solution is spread on a petri dish, solvent is evaporated for drying to give a membrane L of composition. In this case, when compound XII and PES are chosen so that [amount of substance of oxocarbons (mmol)] [weight (g) of polymer electrolyte+weight (g) of oxocarbons] of membrane L is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

EXAMPLE 12

A flask is charged with compound XIII that $X^1$, $X^2$, Z, n and R in the formula (1) are shown in Table 4, PES and a mixed liquid of methylene chloride:methanol=9:1 (vol/vol), stirred to obtain a uniform solution. This solution is spread on a petri dish, solvent is evaporated for drying to give a membrane M of composition. In this case, when compound G and PES are chosen so that [amount of substance of oxocarbons (mmol)]/[weight (g) of polymer electrolyte+weight (g) of oxocarbons] of membrane M is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

EXAMPLE 13

A flask is charged with compound XIII that $X^1$, $X^2$, Z, n and R in the formula (1) are shown in Table 4, PES and a mixed liquid of methylene chloride:methanol=9:1 (vol/vol), stirred to obtain a uniform solution. This solution is spread on a petri dish, solvent is evaporated for drying to give a membrane N of composition. In this case, when compound XIII and PES are chosen so that [amount of substance of oxocarbons (mmol)]/[weight (g) of polymer electrolyte+weight (g) of oxocarbons] of membrane N is in a range of 0.05 to 8 mmol/g, there is preferably obtained a membrane with proton conductivity equal to a polymer compound having a sulfonic acid group, and also with excellent chemical stability and water resistance compared with the polymer compound having a sulfonic acid group.

REFERENCE EXAMPLE 4

To a flask equipped with an azeotropic distillation apparatus, under Ar atmosphere, were added 25.0 g (110 mmol) of potassium 2,5-dihydroxybenzenesulfonate, 60.2 g (123 mmol) of dipotassium 4,4'-difluorodiphenylsulfone-3,3'-disulfonate and 15.9 g (115 mmol) of potassium carbonate, 341 mL of DMSO and 68 mL of toluene were added thereto. Thereafter, water in the system was subjected to azeotropic dehydration by distilling toluene away at a bath temperature of 150° C., stirred under the constant temperature of 150° C. for 6.5 hours, thereby to give a hydrophilic oligomer solution (b1). To another flask equipped with an azeotropic distillation apparatus, under Ar atmosphere, were added 78.2 g (312 mmol) of 4,4'-dihydroxydipheylsulfone, 76.1 g (299 mmol) of 4,4'-difluorodipheylsulfone and 47.5 g (344 mmol) of potassium carbonate, 617 mL of DMSO and 123 mL of toluene were added thereto. Thereafter, water in the system was subjected to azeotropic dehydration by distilling toluene away at a bath temperature of 150° C., stirred under the constant temperature of 150° C. for 6.5 hours, thereby to give a hydrophobic oligomer solution (b2).

Subsequently, after the reaction liquid was allowed to stand sufficiently to room temperature, the hydrophilic oligomer solution obtained was added to the hydrophobic oligomer solution, and while raising temperature to 150° C., stirred under heating for 18 hours in total. The reaction liquid was cooled, then, added dropwise into a large amount of aqueous hydrochloric acid solution, the resultant precipitate was collected by filtration. Further, the precipitate was repeatedly washed with water until the filtrate became neutral, and washed with hot water of 100° C. for 2 hours, filtrated and dried, thereby to give 194 g of polymer b. The ion exchange capacity of the polymer b was 1.36 meq/g.

EXAMPLE 14

A flask was charged with 0.265 g of the polymer b synthesized in Reference example 4, 0.142 g of compound II and 10 ml of a mixed liquid of methylene chloride:methanol=9:1 (vol/vol), stirred to obtain a uniform solution. This solution was spread on a petri dish, solvent is evaporated for drying at normal temperature and pressure to give a membrane 0 of composition. The value of [amount of substance of oxocarbons (mmol)]/[weight (g) of polymer electrolyte+weight (g) of oxocarbons] of membrane 0 was 2.00 (mmol/g). Table 3 shows the test result on tensile strength and measurement result on proton conductivity of the membrane O.

COMPARATIVE EXAMPLE 2

A flask was charged with 0.400 g of the polymer b synthesized in Reference example 4 and 10 ml of a mixed liquid of methylene chloride:methanol=9:1 (vol/vol), stirred to obtain a uniform solution. This solution is spread on a petri dish, solvent was evaporated for drying at normal temperature and pressure to give a polymer electrolyte membrane P. Table 3 shows the test result on tensile strength and measurement result on proton conductivity of the membrane P.

EXAMPLE 15

To a flask equipped with an azeotropic distillation apparatus, under Ar atmosphere, were added 9.32 parts by weight of dipotassium 4,4'-difluorodiphenylsulfone-3,3'-disulfonate, 4.20 parts by weight of potassium 2,5-dihydroxybenzenesulfonate, 59.6 parts by weight of DMSO and 9.00 parts by weight of toluene, and while these were stirred at room temperature, the contents of flask were allowed to bubble with argon gas for 1 hour. Thereafter, 2.67 parts by weight of potassium carbonate was added to the resultant mixture, was subjected to azeotropic dehydration by stirring at 140° C. Then, heating was continued while toluene was distilled away, thereby to give a hydrophilic oligomer solution (c1). The total heating time was 14 hours. The solution obtained was allowed to stand at room temperature.

To another flask equipped with an azeotropic distillation apparatus, under Ar atmosphere, were added 8.32 parts by weight of 4,4'-difluorodiphenylsulfone, 5.36 parts by weight of 2,6-dihydroxynaphthalene, 30.2 parts by weight of DMSO, 30.2 parts by weight of NMP and 9.81 parts by weight of toluene, and while these were stirred at room temperature, the contents of flask were allowed to bubble with argon gas for 1 hour. Thereafter, 5.09 parts by weight of potassium carbonate was added to the resultant mixture, was subjected to azeotropic dehydration by stirring at 140° C. Then, heating was continued while toluene was distilled away. The total heating time was 5 hours. The solution obtained was allowed to stand at room temperature, thereby to give a hydrophobic oligomer solution (c2).

To the hydrophobic oligomer solution (c2) obtained, the whole of the above-described hydrophilic oligomer solution (c1), 80.4 parts by weight of NMP and 45.3 parts by weight of DMSO were added, and subjected to a block copolymerization reaction at 150° C. for 40 hours.

The resultant reaction liquid was added dropwise into a large amount of 2N hydrochloric acid and immersed therein for 1 hour. Thereafter, the generated precipitate was collected by filtration, then immersed again in 2N hydrochloric acid for 1 hour. The precipitate obtained was collected by filtration, washed with water, then, immersed in a large amount of hot water of 95° C. for 1 hour. This solution was dried at 80° C. for 12 hours, thereby synthesizing poly[oxy(2-sulfo-1,4-phenylene)oxy(2-sulfo-1,4-phenylene)su lfonyl(3-sulfo-1,4-phenylene)]-block-poly(oxy-2,6-naphthyle neoxy-1,4-phenylenesulfonyl-1,4-phenylene) (polymer c). The ion exchange capacity of the polymer c was 2.20 meq/g. A flask was charged with 0.266 g of polymer c, 0.141 g of compound I and 5 g of NMP, stirred to obtain a uniform solution. This solution was spread on a petri dish, solvent was evaporated for drying at 80° C. under normal pressure to give a membrane Q of composition. The value of [amount of substance of oxocarbons (mmol)]/[weight (g) of polymer electrolyte+weight (g) of oxocarbons] of membrane Q was 3.04 (mmol/g). Table 3 shows the test result on tensile strength and measurement result on proton conductivity of the membrane Q.

COMPARATIVE EXAMPLE 3

A flask was charged with 0.400 g of polymer c and 5 g of NMP to obtain a uniform solution. This solution was spread on a petri dish, solvent was evaporated for drying at 80° C. under normal pressure to give a polymer electrolyte membrane R. Table 3 shows the test result on tensile strength and measurement result on proton conductivity of the membrane R.

EXAMPLE 16

To a flask equipped with an azeotropic distillation apparatus, under Ar atmosphere, were added 145 parts by weight of DMSO, 56.6 parts by weight of toluene, 5.66 parts by weight of sodium 2,5-dichlorobenzenesulfonate, 2.13 parts by weight of polyethersulfone of chloro-terminal type (Sumika Excel PES 5200P manufactured by Sumitomo Chemical CO., Ltd.) and 9.35 parts by weight of 2,2'-bipyridyl, followed by stirring. Thereafter, a bath temperature was raised to 150° C., water in the system was subjected to azeotropic dehydration by thermally distilling toluene away, then, cooled to 60° C. Next, 15.7 parts by weight of bis(1,5-cyclooctadiene)nickel (0) was added thereto, temperature was raised to 80° C., and stirred for 5 hours at the temperature. After being cooled, the reaction liquid was poured into a large amount of 6 mol/L hydrochloric acid for a polymer to precipitate and to be filtered. Thereafter, the washing/filtering was repeated with 6 mol/L hydrochloric acid several times, then washing with water was conducted until the filtrate became neutral, followed by drying under reduced pressure, thereby synthesizing poly(sufo-1,4-phenylene)-block-poly(oxy-1,4-phenylenesulfon yl-1,4-phenylene) (polymer d). The ion exchange capacity of the polymer d was 2.20 meq/g. A flask was charged with 0.266 g of polymer d, 0.141 g of compound I and 5 g of NMP, stirred to obtain a uniform solution. This solution was spread on a petri dish, solvent was evaporated for drying at 80° C. under normal pressure to give a membrane S of composition. The value of [amount of substance of oxocarbons (mmol)]/[weight (g) of polymer electrolyte+weight (g) of oxocarbons] of membrane S was 3.04 (mmol/g). Table 3 shows the test result on tensile strength and measurement result on proton conductivity of the membrane S.

COMPARATIVE EXAMPLE 4

A flask was charged with 0.400 g of polymer d and 5 g of NMP to obtain a uniform solution. This solution was spread on a petri dish, solvent was evaporated for drying at 80° C. under normal pressure to give a polymer electrolyte membrane T. Table 3 shows the test result on tensile strength and measurement result on proton conductivity of the membrane T.

EXAMPLE 17

In accordance with a method described in Polymer Communications, 1984, Vol. 25, 93-96, and Macromolecules, 1980, 13, 1325-1332, poly(diphenoxy)phosphazene (polymer e) was synthesized. 3.10 g of the polymer e was dissolved in 30 ml of concentrated sulfuric acid, followed by reaction at 50° C. for 8 hours, then, the resultant solution was added dropwise into iced water, thereby synthesizing sulfonated product of poly(diphenoxy)phosphazene (polymer f). The ion exchange capacity of the polymer f was 1.30 meq/g. A flask was charged with 0.503 g of polymer f, 0.146 g of compound I and 10 g of NMP, stirred to obtain a uniform solution. This solution was spread on a petri dish, solvent was evaporated for drying at 80° C. under normal pressure to give a membrane U of composition. The value of [amount of substance of oxocarbons (mmol)]/[weight (g) of polymer electrolyte+weight (g) of oxocarbons] of membrane U was 1.97 (mmol/g). Table 3 shows the test result on tensile strength and measurement result on proton conductivity of the membrane U.

COMPARATIVE EXAMPLE 5

A flask was charged with 0.400 g of polymer f and 5 g of NMP to obtain a uniform solution. This solution was spread on a petri dish, solvent was evaporated for drying at 80° C. under normal pressure to give a polymer electrolyte membrane V. Table 3 shows the test result on tensile strength and measurement result on proton conductivity of the membrane V.

EXAMPLE 18

A flask was charged with 10.36 g (polymer amount of 0.518 g) of 5 wt % Nafion solution (manufactured by Aldrich Corporation) and 0.142 g of compound II, stirred to obtain a uniform solution. This solution was spread on a petri dish, solvent was evaporated for drying at 80° C. under normal pressure to give a membrane W of composition. The value of [amount of substance of oxocarbons (mmol)]/[weight (g) of polymer electrolyte+weight (g) of oxocarbons] of membrane W was 1.24 (mmol/g). Table 3 shows the test result on tensile strength and measurement result on proton conductivity of the membrane W.

COMPARATIVE EXAMPLE 6

5 wt % Nafion solution (manufactured by Aldrich Corporation) was spread on a petri dish, solvent was evaporated for drying at 80° C. under normal pressure to give a polymer electrolyte membrane X. Table 3 shows the test result on tensile strength and measurement result on proton conductivity of the membrane X.

EXAMPLE 19

A flask is charged with compound VIII that $X^1$, $X^2$, Z, n and R in the formula (1) are shown in Table 4, polymer b and DMAc, stirred to obtain a uniform solution. This solution is spread on a petri dish, solvent is evaporated for drying to give a membrane Y of composition. In this case, when compound VIII and polymer b are chosen so that [amount of substance of oxocarbons (mmol)]/[weight (g) of polymer electrolyte+weight (g) of oxocarbons] of membrane Y is in a range of 0.05 to 8 mmol/g, there is preferably obtained a membrane with extremely high flexibility compared with a single polymer electrolyte without lowering the proton conductivity so much.

EXAMPLE 20

A flask is charged with compound IX that $X^1$, $X^2$, Z, n and R in the formula (1) are shown in Table 4, polymer c and NMP, stirred to obtain a uniform solution. This solution is spread on a petri dish, solvent is evaporated for drying to give a membrane Z of composition. In this case, when compound IX and polymer c are chosen so that [amount of substance of oxocarbons (mmol)]/[weight (g) of polymer electrolyte+weight (g) of oxocarbons] of membrane Z is in a range of 0.05 to 8 mmol/g, there is preferably obtained a membrane with extremely high flexibility compared with a single polymer electrolyte without lowering the proton conductivity so much.

EXAMPLE 21

A flask is charged with compound X that $X^1$, $X^2$, Z, n and R in the formula (1) are shown in Table 4, polymer d and DMSO, stirred to obtain a uniform solution. This solution is spread on a petri dish, solvent is evaporated for drying to give a membrane AA of composition. In this case, when compound X and polymer d are chosen so that [amount of substance of oxocarbons (mmol)]/[weight (g) of polymer electrolyte+weight (g) of oxocarbons] of membrane AA is in a range of 0.05 to 8 mmol/g, there is preferably obtained a membrane with extremely high flexibility compared with a single polymer electrolyte without lowering the proton conductivity so much.

EXAMPLE 22

A flask is charged with compound XI that $X^1$, $X^2$, Z, n and R in the formula (1) are shown in Table 4, polymer b and DMAc, stirred to obtain a uniform solution. This solution is spread on a petri dish, solvent is evaporated for drying to give a membrane AB of composition. In this case, when compound XI and polymer b are chosen so that [amount of substance of oxocarbons (mmol)]/[weight (g) of polymer electrolyte+weight (g) of oxocarbons] of membrane AB is in a range of 0.05 to 8 mmol/g, there is preferably obtained a membrane with extremely high flexibility compared with a single polymer electrolyte without lowering the proton conductivity so much.

EXAMPLE 23

A flask is charged with compound V that $X^1$, $X^2$, Z, n and R in the formula (1) are shown in Table 4, polymer c and NMP, stirred to obtain a uniform solution. This solution is spread on a petri dish, solvent is evaporated for drying to give a membrane AC of composition. In this case, when compound V and polymer c are chosen so that [amount of substance of oxocarbons (mmol)]/[weight (g) of polymer electrolyte+weight (g) of oxocarbons] of membrane AC is in a range of 0.05 to 8 mmol/g, there is preferably obtained a membrane with extremely high flexibility compared with a single polymer electrolyte without lowering the proton conductivity so much.

EXAMPLE 24

A flask is charged with compound VII that $X^1$, $X^2$, Z, n and R in the formula (1) are shown in Table 4, polymer d and DMSO, stirred to obtain a uniform solution. This solution is spread on a petri dish, solvent is evaporated for drying to give a membrane AD of composition. In this case, when compound VII and polymer d are chosen so that [amount of substance of oxocarbons (mmol)]/[weight (g) of polymer electrolyte+weight (g) of oxocarbons] of membrane AD is in a range of 0.05 to 8 mmol/g, there is preferably obtained a membrane with extremely high flexibility compared with a single polymer electrolyte without lowering the proton conductivity so much.

EXAMPLE 25

A flask is charged with compound XII that $X^1$, $X^2$, Z, n and R in the formula (1) are shown in Table 4, polymer b and DMAc, stirred to obtain a uniform solution. This solution is spread on a petri dish, solvent is evaporated for drying to give a membrane AE of composition. In this case, when compound XII and polymer b are chosen so that [amount of substance of oxocarbons (mmol)]/[weight (g) of polymer electrolyte+weight (g) of oxocarbons] of membrane AE is in a range of 0.05 to 8 mmol/g, there is preferably obtained a membrane with extremely high flexibility compared with a single polymer electrolyte without lowering the proton conductivity so much.

EXAMPLE 26

A flask is charged with compound XIII that $X^1$, $X^2$, Z, n and R in the formula (1) are shown in Table 4, polymer c and NMP, stirred to obtain a uniform solution. This solution is spread on a petri dish, solvent is evaporated for drying to give a membrane AF of composition. In this case, when compound XIII and polymer c are chosen so that [amount of substance of oxocarbons (mmol)]/[weight (g) of polymer electrolyte+weight (g) of oxocarbons] of membrane AF is in a range of 0.05 to 8 mmol/g, there is preferably obtained a membrane with extremely high flexibility compared with a single polymer electrolyte without lowering the proton conductivity so much.

EXAMPLE 27

A flask is charged with compound XIII that $X^1$, $X^2$, Z, n and R in the formula (1) are shown in Table 4, polymer d and DMSO, stirred to obtain a uniform solution. This solution is spread on a petri dish, solvent is evaporated for drying to give a membrane AG of composition. In this case, when compound XIII and polymer d are chosen so that [amount of substance of oxocarbons (mmol)]/[weight (g) of polymer electrolyte+weight (g) of oxocarbons] of membrane AG is in a range of 0.05 to 8 mmol/g, there is preferably obtained a membrane with extremely high flexibility compared with a single polymer electrolyte without lowering the proton conductivity so much.

TABLE 1

| Temperature & Humidity conditions | Proton conductivity (S/cm) 80° C., 70% RH |
|---|---|
| Example 1 (A) | $1.2 \times 10^{-3}$ |
| Example 5 (F) | $2.1 \times 10^{-3}$ |

TABLE 1-continued

| Temperature & Humidity conditions | Proton conductivity (S/cm) 80° C., 70% RH |
|---|---|
| Example 6 (G) | $3.5 \times 10^{-3}$ |
| Comparative Example 1 (E) | $3.6 \times 10^{-3}$ |

(Table 1: Measurement of Proton Conductivity Under Humidification)

TABLE 2

| Temperature & Humidity conditions | Proton conductivity (S/cm) | | |
|---|---|---|---|
| | 120° C., 0% RH | 130° C., 0% RH | 140° C., 0% RH |
| Example 2 (B) | $1.2 \times 10^{-5}$ | $1.6 \times 10^{-5}$ | $2.3 \times 10^{-5}$ |
| Example 3 (C) | $7.1 \times 10^{-5}$ | $9.9 \times 10^{-5}$ | $1.3 \times 10^{-4}$ |
| Example 4 (D) | $1.3 \times 10^{-5}$ | $1.7 \times 10^{-5}$ | $2.6 \times 10^{-5}$ |
| Comparative Example 1 (E) | Measurement limit ($1.0 \times 10^{-7}$) or less | Measurement limit ($1.0 \times 10^{-7}$) or less | Measurement limit ($1.0 \times 10^{-7}$) or less |

(Table 2: Measurement of Proton Conductivity Under No Humidification)

TABLE 3

| | Tensile test | | Proton conductivity (S/cm) Temperature: 80° C., Relative humidity: 90% RH |
|---|---|---|---|
| | Modulus (Mpa) | Breaking strain (%) | |
| Example 14 (O) | 515 | 55 | $7.1 \times 10^{-2}$ |
| Comparative Example 2 (P) | 1330 | 8.9 | $6.4 \times 10^{-2}$ |
| Example 15 (Q) | 59 | 57 | $5.9 \times 10^{-2}$ |
| Comparative Example 3 (R) | 700 | 49 | $1.6 \times 10^{-1}$ |
| Example 16 (S) | 910 | 34 | $5.9 \times 10^{-2}$ |
| Comparative Example 4 (T) | 1200 | 16 | $5.8 \times 10^{-2}$ |
| Example 17 (U) | 7 | 410 | $2.2 \times 10^{-2}$ |
| Comparative Example 5 (V) | 250 | 49 | $6.4 \times 10^{-2}$ |
| Example 18 (W) | 92 | 47 | $7.3 \times 10^{-2}$ |
| Comparative Example 6 (X) | 160 | 80 | $1.3 \times 10^{-1}$ |

(Table 3: Tensile Test and Proton Conductivity Measurement)

TABLE 4

| | $X^1, X^2$ | Z | n | R |
|---|---|---|---|---|
| Compound I | O | —CO— | 1 | —OH |
| Compound II | O | —CO— | 1 | 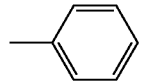 |
| Compound VIII | O | —CO— | 2 | —OH |
| Compound IX | O | —CO— | 0 | —OH |
| Compound X | S | —C(S)— | 1 | —SH |
| Compound XI | N | —C(NH)— | 1 | —NH$_2$ |
| Compound V | O | —CO— | 1 | 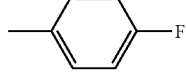 |
| Compound VII | O | —CO— | 1 | 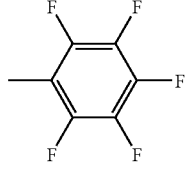 |
| Compound XII | O | —CO— | 1 | 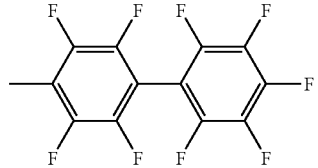 |
| Compound XIII | O | —CO— | 1 | 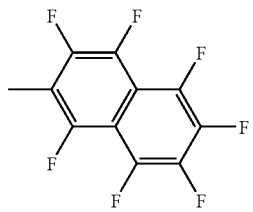 |

TABLE 4-continued

| | $X^1, X^2$ | Z | n | R |
|---|---|---|---|---|
| Compound XIIII | O | —CO— | 1 | 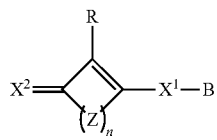 |

INDUSTRIAL APPLICABILITY

The composition containing a polymer and an oxocarbon of the present invention is useful as a material for proton conductive membrane, i.e., polymer electrolyte of a solid polymer type fuel cell using gas fuels such as hydrogen gas and liquid fuels such as methanol and dimethyl ether. In particular, the composition of the present invention not only has proton conductivity equal to a single polymer electrolyte but also its membrane has flexibility effective in stress relaxation compared with a single polymer electrolyte, thus it is advantageous in practical aspects like durability.

The invention claimed is:

1. A polymer composition comprising an oxocarbon and a polymer, wherein
the polymer is selected from the group consisting of polyvinyl pyrrolidones, polyesters, polyvinyl pyridines, polybenzimidazoles, polyethersulfones, a copolymer thereof and a mixture thereof, and
wherein the oxocarbon is expressed by the following formula (1):

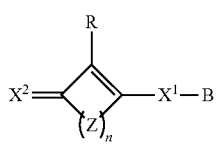

(1)

wherein $X^1$ and $X^2$ each independently represent —O—, —S— or —NR'—, Z represents —CO—, —C(S)—, —C(NR")—, an alkylene group having carbon atoms of 1-6 that may have a substituent, or an arylene group having carbon atoms of 6-10 that may have a substituent; n represents the number of Z and an integer of 0 (inclusive) to 10; when Z are plural, each of Z may be the same or different each other; R represents —OH, —SH, —NHR'", an alkyl group having carbon atoms of 1-18 that may have a substituent, an aryl group having carbon atoms of 6-18 that may have a substituent, or an aralkyl group having carbon atoms of 7-16 that may have a substituent; R', R" and R'" each independently represent a hydrogen atom, an alkyl group having carbon atoms of 1-6 that may have a substituent, or an aryl group having carbon atoms of 6-10 that may have a substituent; and B represents a hydrogen atom or a monovalent metal atom.

2. The polymer composition of claim 1, wherein Z is any one of —CO—, —C(S)— and —C(NH)—.

3. The polymer composition of claim 2, wherein Z is —CO—.

4. The polymer composition of claim 1, wherein $X^1$ is —O—.

5. The polymer composition of claim 1, wherein $X^2$ is —O—.

6. The polymer composition of claim 1, wherein both $X^1$ and $X^2$ are —O—.

7. The polymer composition of claim 4, wherein n is an integer of 0 to 2.

8. The polymer composition of claim 5, wherein n is an integer of 0 to 2.

9. The polymer composition of claim 6, wherein n is an integer of 0 to 2.

10. The polymer composition of claim 1, wherein [amount of substance of oxocarbons (mmol)]/[weight (g) of polymer+ weight (g) of oxocarbons] is 0.05 to 8 mmol/g.

11. A polymer electrolyte comprising the polymer composition of claim 1 as an active constituent.

12. A polymer electrolyte membrane comprising an oxocarbon and a polymer electrolyte.

13. A polymer electrolyte membrane-electrode assembly comprising a polymer electrolyte comprising a polymer composition comprising an oxocarbon and a polymer.

14. A battery comprising a polymer electrolyte comprising a polymer composition comprising an oxocarbon and a polymer.

15. An oxocarbon compound wherein R of the compound expressed by the following general formula (1) is a halogeno-substituted aryl group:

(1)

wherein $X^1$ and $X^2$ each independently represent —O—, —S— or —NR'—, Z represents —CO—, —C(S)—, —C(NR")—, an alkylene group having carbon atoms of 1-6 that may have a substituent, or an arylene group having carbon atoms of 6-10 that may have a substituent; n represents the number of Z and an integer of 0 (inclusive) to 10; when Z are plural, each of Z may be the same or different each other; R represents —OH, —SH, —NHR'", an alkyl group having carbon atoms of 1-18 that may have a substituent, or an aralkyl group having carbon atoms of 7-16 that may have a substituent; R', R" and R'" each independently represent a hydrogen atom, an alkyl group having carbon atoms of 1-6 that may have a substituent, or an aryl group having carbon atoms of 6-10 that may have a substituent; and B represents a hydrogen atom or a monovalent metal atom.

16. The oxocarbon compound of claim 15 wherein the halogeno-substituted aryl group is a group selected from the group consisting of the following formulas (2a) to (2c):

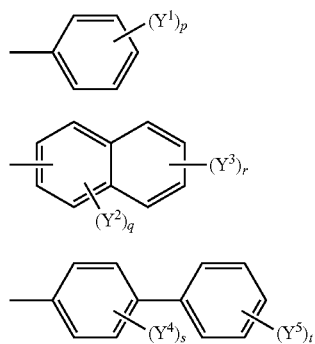

(2a)

(2b)

(2c)

wherein p represents an integer of 1 to 5, q represents an integer of 0 (inclusive) to 3, r represents an integer of 0 (inclusive) to 4, and a value of (q+r) is 1 to 7, s represents an integer of 0 (inclusive) to 4, t represents an integer of 0 (inclusive) to 5, and a value of (s+t) is 1 to 9; $Y^1$ to $Y^5$ each independently represents a halogeno group, when $Y^1$ to $Y^5$ are each plural, these may be same or different.

17. The oxocarbon compound of claim 16, wherein the halogeno group is a fluoro group.

18. The oxocarbon compound of claim 17, wherein the halogeno-substituted aryl group is (2a).

19. The oxocarbon compound of claim 18 expressed by the following formula (3):

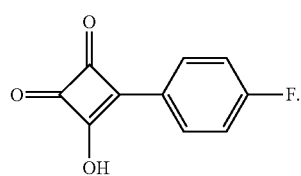

(3)

20. The oxocarbon compound of claim 18 expressed by the following formula (4):

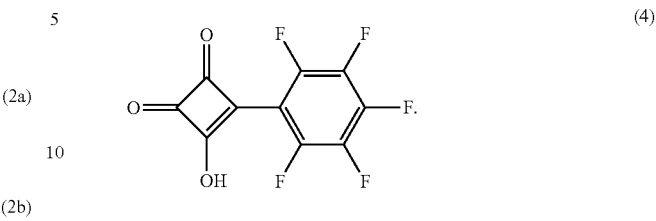

(4)

21. A polymer electrolyte membrane-electrode assembly comprising a polymer electrolyte membrane comprising an oxocarbon and a polymer electrolyte.

22. A battery comprising a polymer electrolyte membrane comprising an oxocarbon and a polymer electrolyte.

23. A battery comprising a polymer electrolyte membrane-electrode assembly comprising a polymer electrolyte comprising a polymer composition comprising an oxocarbon and a polymer.

24. A polymer electrolyte comprising the polymer composition of claim 2 as an active constituent.

25. A polymer electrolyte comprising the polymer composition of claim 3 as an active constituent.

26. A polymer electrolyte comprising the polymer composition of claim 4 as an active constituent.

27. A polymer electrolyte comprising the polymer composition of claim 5 as an active constituent.

28. A polymer electrolyte comprising the polymer composition of claim 6 as an active constituent.

29. A polymer electrolyte comprising the polymer composition of claim 7 as an active constituent.

30. A polymer electrolyte comprising the polymer composition of claim 8 as an active constituent.

31. A polymer electrolyte comprising the polymer composition of claim 9 as an active constituent.

* * * * *